United States Patent
Yang et al.

(10) Patent No.: US 10,155,967 B2
(45) Date of Patent: *Dec. 18, 2018

(54) MICROORGANISM HAVING ENHANCED PRODUCTIVITY OF LACTIC ACID AND A PROCESS FOR PRODUCING LACTIC ACID USING THE SAME

(71) Applicant: CJ Cheiljedang Corporation, Seoul (KR)

(72) Inventors: Eun Bin Yang, Seoul (KR); Tae Hee Lee, Gyeonggi-do (KR); Seon Hye Kim, Gyeonggi-do (KR); Gyuhyeon Song, Daejeon (KR); Cheol Woong Ha, Seoul (KR); Kyungsu Na, Gyeonggi-do (KR); Young Lyeol Yang, Gyeonggi-do (KR); Min Sun Kang, Jeollanam-do (KR); Hyo Hyoung Lee, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/735,096

(22) PCT Filed: Jun. 12, 2015

(86) PCT No.: PCT/KR2015/005963
§ 371 (c)(1),
(2) Date: Dec. 8, 2017

(87) PCT Pub. No.: WO2016/199966
PCT Pub. Date: Dec. 15, 2016

(65) Prior Publication Data
US 2018/0171370 A1 Jun. 21, 2018

(51) Int. Cl.
| | |
|---|---|
| *C12N 1/14* | (2006.01) |
| *C12P 7/56* | (2006.01) |
| *C12N 1/18* | (2006.01) |
| *C12N 9/02* | (2006.01) |
| *C12N 9/88* | (2006.01) |
| *C12N 9/00* | (2006.01) |

(52) U.S. Cl.
CPC .......... *C12P 7/56* (2013.01); *C12N 1/18* (2013.01); *C12N 9/0008* (2013.01); *C12N 9/88* (2013.01); *C12N 9/93* (2013.01); *C12Y 102/01003* (2013.01); *C12Y 401/01001* (2013.01); *C12Y 602/01001* (2013.01)

(58) Field of Classification Search
CPC .................................. C12P 7/56; C12N 9/0006
USPC ............................ 435/139, 190, 254.2, 471
See application file for complete search history.

(56) References Cited

U.S. PATENT DOCUMENTS

| | | |
|---|---|---|
| 2006/0148050 A1 | 7/2006 | Poro et al. |
| 2010/0248233 A1 | 9/2010 | Muller et al. |
| 2012/0021421 A1 | 1/2012 | Amar et al. |
| 2017/0175150 A1* | 6/2017 | Yang .................. C12P 7/56 |

FOREIGN PATENT DOCUMENTS

| | | |
|---|---|---|
| CN | 104099258 A | 10/2014 |
| KR | 10-2013-0126809 A | 11/2013 |
| KR | 10-2014-0001165 A | 1/2014 |
| KR | 10-2015-0056448 A | 5/2015 |

OTHER PUBLICATIONS

WO2016199966.English translation of the writtenopinion (2016).*
Akamatsu et al. 2000. Effects of aldehyde dehydrogenase and acetyl-CoA synthetase on acetate formation in sake mash. *Journal of Bioscience and Bioengineering*, 90(5):555-560.
Ishida et al. 2014. The effect of pyruvate decarboxylase gene knockout in *Saccharomyces cerevisiae* on L-Lactic acid production. *Bioscience, Biotechnology, and Biochemistry*, 70(5):1148-1153.
Lee et al. 2006. Development of reusable split URA3-marked knockout vectors for *Saccharomyces cerevisiae*, 16(6):979-982.
Liu et al. 2012. Metabolic engineering of biocatalysts for carboxylic acids production. *Computational and Structural Biotechnology Journal*, 3(4):e201210011.
Schüller, H.-J. 2003. Transcriptional control of nonfermentative metabolism in the yeast *Saccharomyces cerevisiae*, *Curr. Genet.*, 43:139-160.
Seeboth et al. 1990. pdc1° $^{Mutants\ of}$ *Saccharomyces cerevisiae* give evidence for an additional structural PDC gene: Cloning of PDC5, a gene homologous to PDC1, *Journal of Bacteriology*, 172(2):678-685.
Tokuhiro et al. 2009. Double mutation of the PDC1 and ADH1 genes improves lactate production in the yeast *Saccharomyces cerevisiae* expressing the bovine lactate dehydrogenase gene. *Appl. Microbiol. Biotechnol.*, 82:883-890.
International Search Report dated Mar. 11, 2016 for International Application No. PCT/KR2015/005963 filed Jun. 12, 2015.
Written Opinion dated Mar. 11, 2016 for International Application No. PCT/KR2015/005963 filed Jun. 12, 2015.

* cited by examiner

*Primary Examiner* — Tekchand Saidha
(74) *Attorney, Agent, or Firm* — Knobbe Martens Olson & Bear LLP

(57) ABSTRACT

The present invention relates to *Saccharomyces* sp. capable of producing lactic acid with a decreased activity of pyruvate decarboxylase (PDC) and increased activities of aldehyde dehydrogenase (ALD) and acetyl-CoA synthetase (ACS), and a method of producing lactic acid from the culture medium obtained by culturing the microorganism.

8 Claims, 2 Drawing Sheets

Specification includes a Sequence Listing.

SEQUENCE LISTING

<160> NUMBER OF SEQ ID NOS: 78

<210> SEQ ID NO 1
<211> LENGTH: 32
<212> TYPE: DNA
<213> ORGANISM: Artificial Sequence
<220> FEATURE:
<223> OTHER INFORMATION: ADH1 upstream forward primer

<400> SEQUENCE: 1
cgggatccac tgtagcccta gacttgatag cc                           32

<210> SEQ ID NO 2
<211> LENGTH: 44
<212> TYPE: DNA
<213> ORGANISM: Artificial Sequence
<220> FEATURE:
<223> OTHER INFORMATION: ADH1 upstream reverse primer

<400> SEQUENCE: 2
ataagaatgc ggccgctgta tatgagatag ttgattgtat gctt              44

<210> SEQ ID NO 3
<211> LENGTH: 37
<212> TYPE: DNA
<213> ORGANISM: Artificial Sequence
<220> FEATURE:
<223> OTHER INFORMATION: ADH1 downstream forward primer

<400> SEQUENCE: 3
gactagtgcg aatttcttat gatttatgat ttttatt                      37

<210> SEQ ID NO 4
<211> LENGTH: 37
<212> TYPE: DNA
<213> ORGANISM: Artificial Sequence
<220> FEATURE:
<223> OTHER INFORMATION: ADH1 downstream reverse primer

<400> SEQUENCE: 4
acatgccatg gaagcatgca cgtatacact tgagtaa                      37

<210> SEQ ID NO 5
<211> LENGTH: 35
<212> TYPE: DNA
<213> ORGANISM: Artificial Sequence
<220> FEATURE:
<223> OTHER INFORMATION: PDC1 upstream forward primer

<400> SEQUENCE: 5
cgggatccat tatgtatgct cttctgactt ttcgt                        35

<210> SEQ ID NO 6
<211> LENGTH: 44
<212> TYPE: DNA
<213> ORGANISM: Artificial Sequence
<220> FEATURE:
<223> OTHER INFORMATION: PDC1 upstream reverse primer

<400> SEQUENCE: 6
ataagaatgc ggccgctttg attgatttga ctgtgttatt ttgc              44

<210> SEQ ID NO 7
<211> LENGTH: 37
<212> TYPE: DNA
<213> ORGANISM: Artificial Sequence

```
<220> FEATURE:
<223> OTHER INFORMATION: PDC1 downstream forward primer

<400> SEQUENCE: 7
cgggatccgc gatttaatct ctaattatta gttaaag                                37

<210> SEQ ID NO 8
<211> LENGTH: 44
<212> TYPE: DNA
<213> ORGANISM: Artificial Sequence
<220> FEATURE:
<223> OTHER INFORMATION: PDC1 downstream reverse primer

<400> SEQUENCE: 8
ataagaatgc ggccgctttc aatcattgga gcaatcattt taca                        44

<210> SEQ ID NO 9
<211> LENGTH: 50
<212> TYPE: DNA
<213> ORGANISM: Artificial Sequence
<220> FEATURE:
<223> OTHER INFORMATION: DLD1-HIS3 upstream linking primer

<400> SEQUENCE: 9
gcgtagttgg ccccaactgg tgcagtaata cgttttaaga gcttggtgag                  50

<210> SEQ ID NO 10
<211> LENGTH: 50
<212> TYPE: DNA
<213> ORGANISM: Artificial Sequence
<220> FEATURE:
<223> OTHER INFORMATION: DLD1-HIS3 downstream linking primer

<400> SEQUENCE: 10
cgtgaagggt gaaaaaggaa aatcagatac ctacataaga acacctttgg                  50

<210> SEQ ID NO 11
<211> LENGTH: 22
<212> TYPE: DNA
<213> ORGANISM: Artificial Sequence
<220> FEATURE:
<223> OTHER INFORMATION: F_PDC5_UP_676

<400> SEQUENCE: 11
gtcagcattg acacgttcga tt                                                22

<210> SEQ ID NO 12
<211> LENGTH: 39
<212> TYPE: DNA
<213> ORGANISM: Artificial Sequence
<220> FEATURE:
<223> OTHER INFORMATION: R_KlURA3-PDC5_UP

<400> SEQUENCE: 12
tctacccaga atcacttctt tcgagagatt gtcataatc                              39

<210> SEQ ID NO 13
<211> LENGTH: 38
<212> TYPE: DNA
<213> ORGANISM: Artificial Sequence
<220> FEATURE:
<223> OTHER INFORMATION: F_PDC5_UP-AL_KlURA3

<400> SEQUENCE: 13
caatctctcg aaagaagtga ttctgggtag aagatcgg                               38
```

<210> SEQ ID NO 14
<211> LENGTH: 27
<212> TYPE: DNA
<213> ORGANISM: Artificial Sequence
<220> FEATURE:
<223> OTHER INFORMATION: R_AL_KlURA3

<400> SEQUENCE: 14
gagcaatgaa cccaataacg aaatctt					27

<210> SEQ ID NO 15
<211> LENGTH: 24
<212> TYPE: DNA
<213> ORGANISM: Artificial Sequence
<220> FEATURE:
<223> OTHER INFORMATION: F_BR_KlURA3

<400> SEQUENCE: 15
cttgacgttc gttcgactga tgag					24

<210> SEQ ID NO 16
<211> LENGTH: 22
<212> TYPE: DNA
<213> ORGANISM: Artificial Sequence
<220> FEATURE:
<223> OTHER INFORMATION: R_PDC5_DOWN_522

<400> SEQUENCE: 16
caagtcaacc aagttagctg gc					22

<210> SEQ ID NO 17
<211> LENGTH: 43
<212> TYPE: DNA
<213> ORGANISM: Artificial Sequence
<220> FEATURE:
<223> OTHER INFORMATION: R_SCO1p-BR_KlURA3

<400> SEQUENCE: 17
ctctcctaat agacgtggtg tcaccatgaa cgacaattct taa					43

<210> SEQ ID NO 18
<211> LENGTH: 38
<212> TYPE: DNA
<213> ORGANISM: Artificial Sequence
<220> FEATURE:
<223> OTHER INFORMATION: F_SCO1p_500

<400> SEQUENCE: 18
cgttcatggt gacaccacgt ctattaggag agccattc					38

<210> SEQ ID NO 19
<211> LENGTH: 41
<212> TYPE: DNA
<213> ORGANISM: Artificial Sequence
<220> FEATURE:
<223> OTHER INFORMATION: R_PDC5_DOWN_500-SCO1p

<400> SEQUENCE: 19
aaggttattt cagacatctt ttctacgttt gctgtttttt c					41

<210> SEQ ID NO 20
<211> LENGTH: 42
<212> TYPE: DNA
<213> ORGANISM: Artificial Sequence
<220> FEATURE:
<223> OTHER INFORMATION: F_SCO1p-PDC5_DOWN_500

```
<400> SEQUENCE: 20
cagcaaacgt agaaaagatg tctgaaataa ccttaggtaa at                          42

<210> SEQ ID NO 21
<211> LENGTH: 44
<212> TYPE: DNA
<213> ORGANISM: Artificial Sequence
<220> FEATURE:
<223> OTHER INFORMATION: R_SCO2p-BR_KlURA3

<400> SEQUENCE: 21
atcgaataag taacaagcgt gtcaccatga acgacaattc ttaa                        44

<210> SEQ ID NO 22
<211> LENGTH: 38
<212> TYPE: DNA
<213> ORGANISM: Artificial Sequence
<220> FEATURE:
<223> OTHER INFORMATION: F_SCO2p_500

<400> SEQUENCE: 22
cgttcatggt gacacgcttg ttacttattc gataacgc                               38

<210> SEQ ID NO 23
<211> LENGTH: 40
<212> TYPE: DNA
<213> ORGANISM: Artificial Sequence
<220> FEATURE:
<223> OTHER INFORMATION: R_PDC5_DOWN_500-SCO2p

<400> SEQUENCE: 23
aaggttattt cagacatttt actctcgctt cccaaattcc                             40

<210> SEQ ID NO 24
<211> LENGTH: 40
<212> TYPE: DNA
<213> ORGANISM: Artificial Sequence
<220> FEATURE:
<223> OTHER INFORMATION: F_SCO2p-PDC5_DOWN_500

<400> SEQUENCE: 24
ggaagcgaga gtaaaatgtc tgaaataacc ttaggtaaat                             40

<210> SEQ ID NO 25
<211> LENGTH: 47
<212> TYPE: DNA
<213> ORGANISM: Artificial Sequence
<220> FEATURE:
<223> OTHER INFORMATION: R_IDP2p-BR_KlURA3

<400> SEQUENCE: 25
taaaaataaa tagatagacg tgtgtcacca tgaacgacaa ttcttaa                     47

<210> SEQ ID NO 26
<211> LENGTH: 42
<212> TYPE: DNA
<213> ORGANISM: Artificial Sequence
<220> FEATURE:
<223> OTHER INFORMATION: F_IDP2p_500

<400> SEQUENCE: 26
cgttcatggt gacacacgtc tatctattta tttttataac tc                          42

<210> SEQ ID NO 27
```

<210> SEQ ID NO 27
<211> LENGTH: 44
<212> TYPE: DNA
<213> ORGANISM: Artificial Sequence
<220> FEATURE:
<223> OTHER INFORMATION: R_PDC5_DOWN_500-IDP2p

<400> SEQUENCE: 27
aaggttattt cagacattac gattttatat atatacgtac gtta        44

<210> SEQ ID NO 28
<211> LENGTH: 45
<212> TYPE: DNA
<213> ORGANISM: Artificial Sequence
<220> FEATURE:
<223> OTHER INFORMATION: F_IDP2p-PDC5_DOWN_500

<400> SEQUENCE: 28
cgtatatata taaaatcgta atgtctgaaa taaccttagg taaat       45

<210> SEQ ID NO 29
<211> LENGTH: 43
<212> TYPE: DNA
<213> ORGANISM: Artificial Sequence
<220> FEATURE:
<223> OTHER INFORMATION: R_ACS1p-BR_KlURA3

<400> SEQUENCE: 29
ctggacgtat gtgcacagtg tcaccatgaa cgacaattct taa         43

<210> SEQ ID NO 30
<211> LENGTH: 38
<212> TYPE: DNA
<213> ORGANISM: Artificial Sequence
<220> FEATURE:
<223> OTHER INFORMATION: F_ACS1p_500

<400> SEQUENCE: 30
cgttcatggt gacactgtgc acatacgtcc agaatgat              38

<210> SEQ ID NO 31
<211> LENGTH: 39
<212> TYPE: DNA
<213> ORGANISM: Artificial Sequence
<220> FEATURE:
<223> OTHER INFORMATION: R_PDC5_DOWN_500-ACS1p

<400> SEQUENCE: 31
aaggttattt cagacatagc acagtgggca atgtctttc             39

<210> SEQ ID NO 32
<211> LENGTH: 41
<212> TYPE: DNA
<213> ORGANISM: Artificial Sequence
<220> FEATURE:
<223> OTHER INFORMATION: F_ACS1p-PDC5_DOWN_500

<400> SEQUENCE: 32
cattgcccac tgtgctatgt ctgaaataac cttaggtaaa t          41

<210> SEQ ID NO 33
<211> LENGTH: 45
<212> TYPE: DNA
<213> ORGANISM: Artificial Sequence
<220> FEATURE:
<223> OTHER INFORMATION: R_FBA1p-BR_KlURA3

<400> SEQUENCE: 33
ttatttacgt aatgacccag tgtcaccatg aacgacaatt cttaa      45

<210> SEQ ID NO 34
<211> LENGTH: 40
<212> TYPE: DNA
<213> ORGANISM: Artificial Sequence
<220> FEATURE:
<223> OTHER INFORMATION: F_FBA1p_500

<400> SEQUENCE: 34
cgttcatggt gacactgggt cattacgtaa ataatgatag      40

<210> SEQ ID NO 35
<211> LENGTH: 44
<212> TYPE: DNA
<213> ORGANISM: Artificial Sequence
<220> FEATURE:
<223> OTHER INFORMATION: R_PDC5_DOWN_500-FBA1p

<400> SEQUENCE: 35
aaggttattt cagacatttt gaatatgtat tacttggtta tggt      44

<210> SEQ ID NO 36
<211> LENGTH: 45
<212> TYPE: DNA
<213> ORGANISM: Artificial Sequence
<220> FEATURE:
<223> OTHER INFORMATION: F_FBA1p-PDC5_DOWN_500

<400> SEQUENCE: 36
ccaagtaata catattcaaa atgtctgaaa taaccttagg taaat      45

<210> SEQ ID NO 37
<211> LENGTH: 41
<212> TYPE: DNA
<213> ORGANISM: Artificial Sequence
<220> FEATURE:
<223> OTHER INFORMATION: F-ALPDC5-BamHI

<400> SEQUENCE: 37
gagctcggat ccaaggaaat aaagcaaata acaataacac c      41

<210> SEQ ID NO 38
<211> LENGTH: 43
<212> TYPE: DNA
<213> ORGANISM: Artificial Sequence
<220> FEATURE:
<223> OTHER INFORMATION: R-ALPDC5-NotI

<400> SEQUENCE: 38
accatggcgg ccgctttgtt cttcttgtta ttgtattgtg ttg      43

<210> SEQ ID NO 39
<211> LENGTH: 42
<212> TYPE: DNA
<213> ORGANISM: Artificial Sequence
<220> FEATURE:
<223> OTHER INFORMATION: F-BRPDC5-SpeI

<400> SEQUENCE: 39
ggatccacta gtgctaatta acataaaact catgattcaa cg      42

<210> SEQ ID NO 40
<211> LENGTH: 42
<212> TYPE: DNA

<213> ORGANISM: Artificial Sequence
<220> FEATURE:
<223> OTHER INFORMATION: R-BRPDC5-NcoI

<400> SEQUENCE: 40
cagctgccat ggtattctaa ataagatgta aggccttgta at                         42

<210> SEQ ID NO 41
<211> LENGTH: 38
<212> TYPE: DNA
<213> ORGANISM: Artificial Sequence
<220> FEATURE:
<223> OTHER INFORMATION: F_PDC1

<400> SEQUENCE: 41
ataactagta tgtctgaaat tactttgggt aaatattt                              38

<210> SEQ ID NO 42
<211> LENGTH: 44
<212> TYPE: DNA
<213> ORGANISM: Artificial Sequence
<220> FEATURE:
<223> OTHER INFORMATION: R_PDC1

<400> SEQUENCE: 42
caaaggaaaa ggggcctgtt tattgcttag cgttggtagc agca                       44

<210> SEQ ID NO 43
<211> LENGTH: 43
<212> TYPE: DNA
<213> ORGANISM: Artificial Sequence
<220> FEATURE:
<223> OTHER INFORMATION: F_CYC1t

<400> SEQUENCE: 43
taccaacgct aagcaataaa caggcccctt ttcctttgtc gat                        43

<210> SEQ ID NO 44
<211> LENGTH: 33
<212> TYPE: DNA
<213> ORGANISM: Artificial Sequence
<220> FEATURE:
<223> OTHER INFORMATION: R_CYC1t

<400> SEQUENCE: 44
atactcgagg caaattaaag ccttcgagcg tcc                                   33

<210> SEQ ID NO 45
<211> LENGTH: 33
<212> TYPE: DNA
<213> ORGANISM: Artificial Sequence
<220> FEATURE:
<223> OTHER INFORMATION: F_PDC1p

<400> SEQUENCE: 45
aaagagctcc atgcgactgg gtgagcatat gtt                                   33

<210> SEQ ID NO 46
<211> LENGTH: 37
<212> TYPE: DNA
<213> ORGANISM: Artificial Sequence
<220> FEATURE:
<223> OTHER INFORMATION: R_PDC1p

<400> SEQUENCE: 46
ataactagtt ttgattgatt tgactgtgtt attttgc                               37

<210> SEQ ID NO 47
<211> LENGTH: 37
<212> TYPE: DNA
<213> ORGANISM: Artificial Sequence
<220> FEATURE:
<223> OTHER INFORMATION: F_IDP2p

<400> SEQUENCE: 47
aaagagctca cgtctatcta tttatttta taactcc                                37

<210> SEQ ID NO 48
<211> LENGTH: 37
<212> TYPE: DNA
<213> ORGANISM: Artificial Sequence
<220> FEATURE:
<223> OTHER INFORMATION: R_IDP2p

<400> SEQUENCE: 48
ataactagtt acgattttat atatatacgt acgttac                               37

<210> SEQ ID NO 49
<211> LENGTH: 35
<212> TYPE: DNA
<213> ORGANISM: Artificial Sequence
<220> FEATURE:
<223> OTHER INFORMATION: F_BamHI-PDC5_UP

<400> SEQUENCE: 49
cgggatccag gccaaggaaa taaagcaaat aacaa                                 35

<210> SEQ ID NO 50
<211> LENGTH: 44
<212> TYPE: DNA
<213> ORGANISM: Artificial Sequence
<220> FEATURE:
<223> OTHER INFORMATION: R_NotI-PDC5_UP

<400> SEQUENCE: 50
ataagaatgc ggccgctttg ttcttcttgt tattgtattg tgtt                       44

<210> SEQ ID NO 51
<211> LENGTH: 36
<212> TYPE: DNA
<213> ORGANISM: Artificial Sequence
<220> FEATURE:
<223> OTHER INFORMATION: F_BamHI-PDC5_DOWN

<400> SEQUENCE: 51
cgggatccgc taattaacat aaaactcatg attcaa                                36

<210> SEQ ID NO 52
<211> LENGTH: 44
<212> TYPE: DNA
<213> ORGANISM: Artificial Sequence
<220> FEATURE:
<223> OTHER INFORMATION: R_NotI-PDC5_DOWN

<400> SEQUENCE: 52
ataagaatgc ggccgctatt ctaaataaga tgtaaggcct tgta                       44

<210> SEQ ID NO 53
<211> LENGTH: 27
<212> TYPE: DNA
<213> ORGANISM: Artificial Sequence
<220> FEATURE:

```
<223> OTHER INFORMATION: F_PDC5_UP

<400> SEQUENCE: 53
aggccaagga aataaagcaa ataacaa                                              27

<210> SEQ ID NO 54
<211> LENGTH: 27
<212> TYPE: DNA
<213> ORGANISM: Artificial Sequence
<220> FEATURE:
<223> OTHER INFORMATION: R_AL_KlURA3

<400> SEQUENCE: 54
gagcaatgaa cccaataacg aaatctt                                              27

<210> SEQ ID NO 55
<211> LENGTH: 24
<212> TYPE: DNA
<213> ORGANISM: Artificial Sequence
<220> FEATURE:
<223> OTHER INFORMATION: F_BR_KlURA3

<400> SEQUENCE: 55
cttgacgttc gttcgactga tgag                                                 24

<210> SEQ ID NO 56
<211> LENGTH: 28
<212> TYPE: DNA
<213> ORGANISM: Artificial Sequence
<220> FEATURE:
<223> OTHER INFORMATION: R_PDC5_DOWN

<400> SEQUENCE: 56
tattctaaat aagatgtaag gccttgta                                             28

<210> SEQ ID NO 57
<211> LENGTH: 35
<212> TYPE: DNA
<213> ORGANISM: Artificial Sequence
<220> FEATURE:
<223> OTHER INFORMATION: F_BamHI-PDC6_UP

<400> SEQUENCE: 57
cgggatcctg ttatagagtt cacaccttat tcaca                                     35

<210> SEQ ID NO 58
<211> LENGTH: 45
<212> TYPE: DNA
<213> ORGANISM: Artificial Sequence
<220> FEATURE:
<223> OTHER INFORMATION: R_NotI-PDC6_UP

<400> SEQUENCE: 58
ataagaatgc ggccgctttg ttggcaatat gtttttgcta tatta                          45

<210> SEQ ID NO 59
<211> LENGTH: 34
<212> TYPE: DNA
<213> ORGANISM: Artificial Sequence
<220> FEATURE:
<223> OTHER INFORMATION: F_BamHI-PDC6_DOWN

<400> SEQUENCE: 59
cgggatccgc cattagtagt gtactcaaac gaat                                      34
```

```
<210> SEQ ID NO 60
<211> LENGTH: 43
<212> TYPE: DNA
<213> ORGANISM: Artificial Sequence
<220> FEATURE:
<223> OTHER INFORMATION: R_NotI-PDC6_DOWN

<400> SEQUENCE: 60
ataagaatgc ggccgcgatg cagaatgagc acttgttatt tat          43

<210> SEQ ID NO 61
<211> LENGTH: 27
<212> TYPE: DNA
<213> ORGANISM: Artificial Sequence
<220> FEATURE:
<223> OTHER INFORMATION: F_PDC6_UP

<400> SEQUENCE: 61
tgttatagag ttcacacctt attcaca                            27

<210> SEQ ID NO 62
<211> LENGTH: 27
<212> TYPE: DNA
<213> ORGANISM: Artificial Sequence
<220> FEATURE:
<223> OTHER INFORMATION: R_AL_KlURA3

<400> SEQUENCE: 62
gagcaatgaa cccaataacg aaatctt                            27

<210> SEQ ID NO 63
<211> LENGTH: 24
<212> TYPE: DNA
<213> ORGANISM: Artificial Sequence
<220> FEATURE:
<223> OTHER INFORMATION: F_BR_KlURA3

<400> SEQUENCE: 63
cttgacgttc gttcgactga tgag                               24

<210> SEQ ID NO 64
<211> LENGTH: 27
<212> TYPE: DNA
<213> ORGANISM: Artificial Sequence
<220> FEATURE:
<223> OTHER INFORMATION: R_PDC6_DOWN

<400> SEQUENCE: 64
gatgcagaat gagcacttgt tatttat                            27

<210> SEQ ID NO 65
<211> LENGTH: 50
<212> TYPE: DNA
<213> ORGANISM: Artificial Sequence
<220> FEATURE:
<223> OTHER INFORMATION: F_SpeI_ALD2

<400> SEQUENCE: 65
caagctggcc gctctagaac tagtatgcct accttgtata ctgatatcga   50

<210> SEQ ID NO 66
<211> LENGTH: 50
<212> TYPE: DNA
<213> ORGANISM: Artificial Sequence
<220> FEATURE:
<223> OTHER INFORMATION: R_XhoI_ALD2
```

<400> SEQUENCE: 66
acataactaa ttacatgact cgagttagtt gtccaaagag agatttatgt                50

<210> SEQ ID NO 67
<211> LENGTH: 50
<212> TYPE: DNA
<213> ORGANISM: Artificial Sequence
<220> FEATURE:
<223> OTHER INFORMATION: F_SpeI_ALD3

<400> SEQUENCE: 67
caagctggcc gctctagaac tagtatgcct accttgtata ctgatatcga                50

<210> SEQ ID NO 68
<211> LENGTH: 50
<212> TYPE: DNA
<213> ORGANISM: Artificial Sequence
<220> FEATURE:
<223> OTHER INFORMATION: R_XhoI_ALD3

<400> SEQUENCE: 68
acataactaa ttacatgact cgagttattt atccaatgaa agatccacat                50

<210> SEQ ID NO 69
<211> LENGTH: 46
<212> TYPE: DNA
<213> ORGANISM: Artificial Sequence
<220> FEATURE:
<223> OTHER INFORMATION: F_SpeI_ACS1

<400> SEQUENCE: 69
tccaagctgg ccgctctaga actagtatgt cgccctctgc cgtaca                46

<210> SEQ ID NO 70
<211> LENGTH: 50
<212> TYPE: DNA
<213> ORGANISM: Artificial Sequence
<220> FEATURE:
<223> OTHER INFORMATION: R_EcoRI_ACS1

<400> SEQUENCE: 70
tatcgataag cttgatatcg aattcttaca acttgaccga atcaattaga                50

<210> SEQ ID NO 71
<211> LENGTH: 563
<212> TYPE: PRT
<213> ORGANISM: Saccharomyces cerevisiae PDC1

<400> SEQUENCE: 71

Met Ser Glu Ile Thr Leu Gly Lys Tyr Leu Phe Glu Arg Leu Lys Gln
 1               5                  10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu

```
            100                 105                 110
Leu His His Thr Leu Gly Asn Gly Asp Phe Thr Val Phe His Arg Met
            115                 120                 125
Ser Ala Asn Ile Ser Glu Thr Thr Ala Met Ile Thr Asp Ile Ala Thr
            130                 135                 140
Ala Pro Ala Glu Ile Asp Arg Cys Ile Arg Thr Thr Tyr Val Thr Gln
145                 150                 155                 160
Arg Pro Val Tyr Leu Gly Leu Pro Ala Asn Leu Val Asp Leu Asn Val
                        165                 170                 175
Pro Ala Lys Leu Leu Gln Thr Pro Ile Asp Met Ser Leu Lys Pro Asn
                180                 185                 190
Asp Ala Glu Ser Glu Lys Glu Val Ile Asp Thr Ile Leu Ala Leu Val
            195                 200                 205
Lys Asp Ala Lys Asn Pro Val Ile Leu Ala Asp Ala Cys Cys Ser Arg
210                 215                 220
His Asp Val Lys Ala Glu Thr Lys Lys Leu Ile Asp Leu Thr Gln Phe
225                 230                 235                 240
Pro Ala Phe Val Thr Pro Met Gly Lys Gly Ser Ile Asp Glu Gln His
                        245                 250                 255
Pro Arg Tyr Gly Gly Val Tyr Val Gly Thr Leu Ser Lys Pro Glu Val
                260                 265                 270
Lys Glu Ala Val Glu Ser Ala Asp Leu Ile Leu Ser Val Gly Ala Leu
            275                 280                 285
Leu Ser Asp Phe Asn Thr Gly Ser Phe Ser Tyr Ser Tyr Lys Thr Lys
        290                 295                 300
Asn Ile Val Glu Phe His Ser Asp His Met Lys Ile Arg Asn Ala Thr
305                 310                 315                 320
Phe Pro Gly Val Gln Met Lys Phe Val Leu Gln Lys Leu Leu Thr Thr
                        325                 330                 335
Ile Ala Asp Ala Ala Lys Gly Tyr Lys Pro Val Ala Val Pro Ala Arg
                340                 345                 350
Thr Pro Ala Asn Ala Ala Val Pro Ala Ser Thr Pro Leu Lys Gln Glu
            355                 360                 365
Trp Met Trp Asn Gln Leu Gly Asn Phe Leu Gln Glu Gly Asp Val Val
        370                 375                 380
Ile Ala Glu Thr Gly Thr Ser Ala Phe Gly Ile Asn Gln Thr Thr Phe
385                 390                 395                 400
Pro Asn Asn Thr Tyr Gly Ile Ser Gln Val Leu Trp Gly Ser Ile Gly
                        405                 410                 415
Phe Thr Thr Gly Ala Thr Leu Gly Ala Ala Phe Ala Ala Glu Glu Ile
                420                 425                 430
Asp Pro Lys Lys Arg Val Ile Leu Phe Ile Gly Asp Gly Ser Leu Gln
            435                 440                 445
Leu Thr Val Gln Glu Ile Ser Thr Met Ile Arg Trp Gly Leu Lys Pro
        450                 455                 460
Tyr Leu Phe Val Leu Asn Asn Asp Gly Tyr Thr Ile Glu Lys Leu Ile
465                 470                 475                 480
His Gly Pro Lys Ala Gln Tyr Asn Glu Ile Gln Gly Trp Asp His Leu
                        485                 490                 495
Ser Leu Leu Pro Thr Phe Gly Ala Lys Asp Tyr Glu Thr His Arg Val
                500                 505                 510
Ala Thr Thr Gly Glu Trp Asp Lys Leu Thr Gln Asp Lys Ser Phe Asn
            515                 520                 525
```

```
Asp Asn Ser Lys Ile Arg Met Ile Glu Ile Met Leu Pro Val Phe Asp
        530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 72
<211> LENGTH: 563
<212> TYPE: PRT
<213> ORGANISM: Saccharomyces cerevisiae PDC5

<400> SEQUENCE: 72

```
Met Ser Glu Ile Thr Leu Gly Lys Tyr Leu Phe Glu Arg Leu Ser Gln
  1               5                  10                  15

Val Asn Cys Asn Thr Val Phe Gly Leu Pro Gly Asp Phe Asn Leu Ser
                 20                  25                  30

Leu Leu Asp Lys Leu Tyr Glu Val Lys Gly Met Arg Trp Ala Gly Asn
             35                  40                  45

Ala Asn Glu Leu Asn Ala Ala Tyr Ala Ala Asp Gly Tyr Ala Arg Ile
         50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Glu Val Val Arg Thr Val Val Glu Leu Ile
        195                 200                 205

Lys Asp Ala Lys Asn Pro Val Ile Leu Ala Asp Ala Cys Ala Ser Arg
    210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335
```

```
Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
            355                 360                 365

Trp Met Trp Asn His Leu Gly Asn Phe Leu Arg Glu Gly Asp Ile Val
370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
            405                 410                 415

Phe Thr Val Gly Ala Leu Leu Gly Ala Thr Met Ala Ala Glu Glu Leu
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
            450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
            485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
            515                 520                 525

Asp Asn Ser Lys Ile Arg Met Ile Glu Val Met Leu Pro Val Phe Asp
530                 535                 540

Ala Pro Gln Asn Leu Val Lys Gln Ala Gln Leu Thr Ala Ala Thr Asn
545                 550                 555                 560

Ala Lys Gln

<210> SEQ ID NO 73
<211> LENGTH: 563
<212> TYPE: PRT
<213> ORGANISM: Saccharomyces cerevisiae PDC6

<400> SEQUENCE: 73

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140
```

```
Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
            165                 170                 175

Pro Gly Ser Leu Leu Glu Lys Pro Ile Asp Leu Ser Leu Lys Pro Asn
        180                 185                 190

Asp Pro Glu Ala Glu Lys Glu Val Ile Asp Thr Val Leu Glu Leu Ile
    195                 200                 205

Gln Asn Ser Lys Asn Pro Val Ile Leu Ser Asp Ala Cys Ala Ser Arg
210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
            245                 250                 255

Pro Arg Tyr Gly Gly Val Tyr Val Gly Thr Leu Ser Lys Gln Asp Val
        260                 265                 270

Lys Gln Ala Val Glu Ser Ala Asp Leu Ile Leu Ser Val Gly Ala Leu
    275                 280                 285

Leu Ser Asp Phe Asn Thr Gly Ser Phe Ser Tyr Ser Tyr Lys Thr Lys
290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
            325                 330                 335

Ile Pro Asp Val Val Lys Gly Tyr Lys Ser Val Pro Val Pro Thr Lys
        340                 345                 350

Thr Pro Ala Asn Lys Gly Val Pro Ala Ser Thr Pro Leu Lys Gln Glu
    355                 360                 365

Trp Leu Trp Asn Glu Leu Ser Lys Phe Leu Gln Glu Gly Asp Val Ile
370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
            405                 410                 415

Phe Thr Thr Gly Ala Thr Leu Gly Ala Ala Phe Ala Ala Glu Glu Ile
        420                 425                 430

Asp Pro Asn Lys Arg Val Ile Leu Phe Ile Gly Asp Gly Ser Leu Gln
    435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
            485                 490                 495

Ala Leu Leu Pro Ala Phe Gly Ala Lys Lys Tyr Glu Asn His Lys Ile
        500                 505                 510

Ala Thr Thr Gly Glu Trp Asp Ala Leu Thr Thr Asp Ser Glu Phe Gln
    515                 520                 525

Lys Asn Ser Val Ile Arg Leu Ile Glu Leu Lys Leu Pro Val Phe Asp
530                 535                 540

Ala Pro Glu Ser Leu Ile Lys Gln Ala Gln Leu Thr Ala Ala Thr Asn
545                 550                 555                 560
```

Ala Lys Gln

<210> SEQ ID NO 74
<211> LENGTH: 506
<212> TYPE: PRT
<213> ORGANISM: Saccharomyces cerevisiae ALD2

<400> SEQUENCE: 74

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
                20                  25                  30

Ser Asp Gly Lys Thr Ile Glu Thr Val Asn Pro Ala Thr Gly Glu Pro
            35                  40                  45

Ile Thr Ser Phe Gln Ala Ala Asn Glu Lys Asp Val Asp Lys Ala Val
        50                  55                  60

Lys Ala Ala Arg Ala Ala Phe Asp Asn Val Trp Ser Lys Thr Ser Ser
65                  70                  75                  80

Glu Gln Arg Gly Ile Tyr Leu Ser Asn Leu Leu Lys Leu Ile Glu Glu
                85                  90                  95

Glu Gln Asp Thr Leu Ala Ala Leu Glu Thr Leu Asp Ala Gly Lys Pro
            100                 105                 110

Tyr His Ser Asn Ala Lys Gly Asp Leu Ala Gln Ile Leu Gln Leu Thr
        115                 120                 125

Arg Tyr Phe Ala Gly Ser Ala Asp Lys Phe Asp Lys Gly Ala Thr Ile
    130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Trp Lys Leu Gln Gly Ala Leu Ala Ala Gly Asn Thr Val Ile Ile Lys
            180                 185                 190

Pro Ala Glu Asn Thr Ser Leu Ser Leu Leu Tyr Phe Ala Thr Leu Ile
        195                 200                 205

Lys Lys Ala Gly Phe Pro Pro Gly Val Val Asn Ile Val Pro Gly Tyr
    210                 215                 220

Gly Ser Leu Val Gly Gln Ala Leu Ala Ser His Met Asp Ile Asp Lys
225                 230                 235                 240

Ile Ser Phe Thr Gly Ser Thr Lys Val Gly Gly Phe Val Leu Glu Ala
                245                 250                 255

Ser Gly Gln Ser Asn Leu Lys Asp Val Thr Leu Glu Cys Gly Gly Lys
            260                 265                 270

Ser Pro Ala Leu Val Phe Glu Asp Ala Asp Leu Asp Lys Ala Ile Asp
        275                 280                 285

Trp Ile Ala Ala Gly Ile Phe Tyr Asn Ser Gly Gln Asn Cys Thr Ala
    290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
                325                 330                 335

Asp Pro Phe Asp Glu Lys Cys Ile Val Gly Pro Val Ile Ser Ser Thr
            340                 345                 350

Gln Tyr Asp Arg Ile Lys Ser Tyr Ile Glu Arg Gly Lys Arg Glu Glu
        355                 360                 365

```
Lys Leu Asp Met Phe Gln Thr Ser Glu Phe Pro Ile Gly Gly Ala Lys
        370                 375                 380

Gly Tyr Phe Ile Pro Pro Thr Ile Phe Thr Asp Val Pro Gln Thr Ser
385                 390                 395                 400

Lys Leu Leu Gln Asp Glu Ile Phe Gly Pro Val Val Val Val Ser Lys
                405                 410                 415

Phe Thr Asn Tyr Asp Asp Ala Leu Lys Leu Ala Asn Asp Thr Cys Tyr
                420                 425                 430

Gly Leu Ala Ser Ala Val Phe Thr Lys Asp Val Lys Lys Ala His Met
                435                 440                 445

Phe Ala Arg Asp Ile Lys Ala Gly Thr Val Trp Ile Asn Ser Ser Asn
450                 455                 460

Asp Glu Asp Val Thr Val Pro Phe Gly Gly Phe Lys Met Ser Gly Ile
465                 470                 475                 480

Gly Arg Glu Leu Gly Gln Ser Gly Val Asp Thr Tyr Leu Gln Thr Lys
                485                 490                 495

Ala Val His Ile Asn Leu Ser Leu Asp Asn
                500                 505

<210> SEQ ID NO 75
<211> LENGTH: 506
<212> TYPE: PRT
<213> ORGANISM: Saccharomyces cerevisiae ALD3

<400> SEQUENCE: 75

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
                20                  25                  30

Ser Asp Gly Lys Thr Ile Glu Thr Val Asn Pro Ala Thr Gly Glu Pro
            35                  40                  45

Ile Thr Ser Phe Gln Ala Ala Asn Glu Lys Asp Val Asp Lys Ala Val
        50                  55                  60

Lys Ala Ala Arg Ala Ala Phe Asp Asn Val Trp Ser Lys Thr Ser Ser
65                  70                  75                  80

Glu Gln Arg Gly Ile Tyr Leu Ser Asn Leu Leu Lys Leu Ile Glu Glu
                85                  90                  95

Glu Gln Asp Thr Leu Ala Ala Leu Glu Thr Leu Asp Ala Gly Lys Pro
                100                 105                 110

Phe His Ser Asn Ala Lys Gln Asp Leu Ala Gln Ile Ile Glu Leu Thr
            115                 120                 125

Arg Tyr Tyr Ala Gly Ala Val Asp Lys Phe Asn Met Gly Glu Thr Ile
130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Arg Lys Met Gln Gly Ala Leu Ala Ala Gly Asn Thr Val Ile Ile Lys
                180                 185                 190

Pro Ala Glu Asn Thr Ser Leu Ser Leu Leu Tyr Phe Ala Thr Leu Ile
            195                 200                 205

Lys Lys Ala Gly Phe Pro Pro Gly Val Val Asn Val Ile Pro Gly Tyr
        210                 215                 220

Gly Ser Val Val Gly Lys Ala Leu Gly Thr His Met Asp Ile Asp Lys
225                 230                 235                 240
```

```
Ile Ser Phe Thr Gly Ser Thr Lys Val Gly Gly Ser Val Leu Glu Ala
            245                 250                 255

Ser Gly Gln Ser Asn Leu Lys Asp Ile Thr Leu Glu Cys Gly Gly Lys
            260                 265                 270

Ser Pro Ala Leu Val Phe Glu Asp Ala Asp Leu Asp Lys Ala Ile Glu
            275                 280                 285

Trp Val Ala Asn Gly Ile Phe Phe Asn Ser Gly Gln Ile Cys Thr Ala
290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
            325                 330                 335

Asp Pro Phe Asp Glu Lys Cys Ile Val Gly Pro Val Ile Ser Ser Thr
            340                 345                 350

Gln Tyr Asp Arg Ile Lys Ser Tyr Ile Glu Arg Gly Lys Lys Glu Glu
            355                 360                 365

Lys Leu Asp Met Phe Gln Thr Ser Glu Phe Pro Ile Gly Gly Ala Lys
            370                 375                 380

Gly Tyr Phe Ile Pro Pro Thr Ile Phe Thr Asp Val Pro Glu Thr Ser
385                 390                 395                 400

Lys Leu Leu Arg Asp Glu Ile Phe Gly Pro Val Val Val Ser Lys
            405                 410                 415

Phe Thr Asn Tyr Asp Asp Ala Leu Lys Leu Ala Asn Asp Thr Cys Tyr
            420                 425                 430

Gly Leu Ala Ser Ala Val Phe Thr Lys Asp Val Lys Lys Ala His Met
            435                 440                 445

Phe Ala Arg Asp Ile Lys Ala Gly Thr Val Trp Ile Asn Gln Thr Asn
450                 455                 460

Gln Glu Glu Ala Lys Val Pro Phe Gly Gly Phe Lys Met Ser Gly Ile
465                 470                 475                 480

Gly Arg Glu Ser Gly Asp Thr Gly Val Asp Asn Tyr Leu Gln Ile Lys
            485                 490                 495

Ser Val His Val Asp Leu Ser Leu Asp Lys
            500                 505

<210> SEQ ID NO 76
<211> LENGTH: 713
<212> TYPE: PRT
<213> ORGANISM: Saccharomyces cerevisiae ACS1

<400> SEQUENCE: 76

Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ala Thr Ala
            20                  25                  30

Gln Gln Lys Lys Glu His Glu Tyr Glu His Leu Thr Ser Val Lys Ile
        35                  40                  45

Val Pro Gln Arg Pro Ile Ser Asp Arg Leu Gln Pro Ala Ile Ala Thr
    50                  55                  60

His Tyr Ser Pro His Leu Asp Gly Leu Gln Asp Tyr Gln Arg Leu His
65                  70                  75                  80

Lys Glu Ser Ile Glu Asp Pro Ala Lys Phe Phe Gly Ser Lys Ala Thr
            85                  90                  95

Gln Phe Leu Asn Trp Ser Lys Pro Phe Asp Lys Val Phe Ile Pro Asp
```

-continued

```
               100                 105                 110
Pro Lys Thr Gly Arg Pro Ser Phe Gln Asn Asn Ala Trp Phe Leu Asn
            115                 120                 125

Gly Gln Leu Asn Ala Cys Tyr Asn Cys Val Asp Arg His Ala Leu Lys
        130                 135                 140

Thr Pro Asn Lys Lys Ala Ile Ile Phe Glu Gly Asp Glu Pro Gly Gln
145                 150                 155                 160

Gly Tyr Ser Ile Thr Tyr Lys Glu Leu Leu Glu Glu Val Cys Gln Val
                165                 170                 175

Ala Gln Val Leu Thr Tyr Ser Met Gly Val Arg Lys Gly Asp Thr Val
            180                 185                 190

Ala Val Tyr Met Pro Met Val Pro Glu Ala Ile Ile Thr Leu Leu Ala
        195                 200                 205

Ile Ser Arg Ile Gly Ala Ile His Ser Val Val Phe Ala Gly Phe Ser
210                 215                 220

Ser Asn Ser Leu Arg Asp Arg Ile Asn Asp Gly Asp Ser Lys Val Val
225                 230                 235                 240

Ile Thr Thr Asp Glu Ser Asn Arg Gly Gly Lys Val Ile Glu Thr Lys
                245                 250                 255

Arg Ile Val Asp Asp Ala Leu Arg Glu Thr Pro Gly Val Arg His Val
            260                 265                 270

Leu Val Tyr Arg Lys Thr Asn Asn Pro Ser Val Ala Phe His Ala Pro
        275                 280                 285

Arg Asp Leu Asp Trp Ala Thr Glu Lys Lys Lys Tyr Lys Thr Tyr Tyr
290                 295                 300

Pro Cys Thr Pro Val Asp Ser Glu Asp Pro Leu Phe Leu Leu Tyr Thr
305                 310                 315                 320

Ser Gly Ser Thr Gly Ala Pro Lys Gly Val Gln His Ser Thr Ala Gly
                325                 330                 335

Tyr Leu Leu Gly Ala Leu Leu Thr Met Arg Tyr Thr Phe Asp Thr His
            340                 345                 350

Gln Glu Asp Val Phe Phe Thr Ala Gly Asp Ile Gly Trp Ile Thr Gly
        355                 360                 365

His Thr Tyr Val Val Tyr Gly Pro Leu Leu Tyr Gly Cys Ala Thr Leu
370                 375                 380

Val Phe Glu Gly Thr Pro Ala Tyr Pro Asn Tyr Ser Arg Tyr Trp Asp
385                 390                 395                 400

Ile Ile Asp Glu His Lys Val Thr Gln Phe Tyr Val Ala Pro Thr Ala
                405                 410                 415

Leu Arg Leu Leu Lys Arg Ala Gly Asp Ser Tyr Ile Glu Asn His Ser
            420                 425                 430

Leu Lys Ser Leu Arg Cys Leu Gly Ser Val Gly Glu Pro Ile Ala Ala
        435                 440                 445

Glu Val Trp Glu Trp Tyr Ser Glu Lys Ile Gly Lys Asn Glu Ile Pro
450                 455                 460

Ile Val Asp Thr Tyr Trp Gln Thr Glu Ser Gly Ser His Leu Val Thr
465                 470                 475                 480

Pro Leu Ala Gly Gly Val Thr Pro Met Lys Pro Gly Ser Ala Ser Phe
                485                 490                 495

Pro Phe Phe Gly Ile Asp Ala Val Val Leu Asp Pro Asn Thr Gly Glu
            500                 505                 510

Glu Leu Asn Thr Ser His Ala Glu Gly Val Leu Ala Val Lys Ala Ala
        515                 520                 525
```

```
Trp Pro Ser Phe Ala Arg Thr Ile Trp Lys Asn His Asp Arg Tyr Leu
            530                 535                 540

Asp Thr Tyr Leu Asn Pro Tyr Pro Gly Tyr Tyr Phe Thr Gly Asp Gly
545                 550                 555                 560

Ala Ala Lys Asp Lys Asp Gly Tyr Ile Trp Ile Leu Gly Arg Val Asp
                565                 570                 575

Asp Val Val Asn Val Ser Gly His Arg Leu Ser Thr Ala Glu Ile Glu
                580                 585                 590

Ala Ala Ile Ile Glu Asp Pro Ile Val Ala Glu Cys Ala Val Val Gly
            595                 600                 605

Phe Asn Asp Asp Leu Thr Gly Gln Ala Val Ala Phe Val Val Leu
            610                 615                 620

Lys Asn Lys Ser Ser Trp Ser Thr Ala Thr Asp Asp Glu Leu Gln Asp
625                 630                 635                 640

Ile Lys Lys His Leu Val Phe Thr Val Arg Lys Asp Ile Gly Pro Phe
                645                 650                 655

Ala Ala Pro Lys Leu Ile Ile Leu Val Asp Asp Leu Pro Lys Thr Arg
                660                 665                 670

Ser Gly Lys Ile Met Arg Arg Ile Leu Arg Lys Ile Leu Ala Gly Glu
            675                 680                 685

Ser Asp Gln Leu Gly Asp Val Ser Thr Leu Ser Asn Pro Gly Ile Val
690                 695                 700

Arg His Leu Ile Asp Ser Val Lys Leu
705                 710
```

<210> SEQ ID NO 77
<211> LENGTH: 348
<212> TYPE: PRT
<213> ORGANISM: Saccharomyces cerevisiae ADH1

<400> SEQUENCE: 77

```
Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
```

```
                180               185                190
Ala Met Gly Tyr Arg Val Leu Gly Ile Asp Gly Gly Glu Gly Lys Glu
                195               200                205

Glu Leu Phe Arg Ser Ile Gly Gly Glu Val Phe Ile Asp Phe Thr Lys
        210               215                220

Glu Lys Asp Ile Val Gly Ala Val Leu Lys Ala Thr Asp Gly Gly Ala
225                 230                235                240

His Gly Val Ile Asn Val Ser Val Ser Glu Ala Ile Glu Ala Ser
                    245                250                255

Thr Arg Tyr Val Arg Ala Asn Gly Thr Thr Val Leu Val Gly Met Pro
            260                265                270

Ala Gly Ala Lys Cys Cys Ser Asp Val Phe Asn Gln Val Val Lys Ser
        275                280                285

Ile Ser Ile Val Gly Ser Tyr Val Gly Asn Arg Ala Asp Thr Arg Glu
            290                295                300

Ala Leu Asp Phe Phe Ala Arg Gly Leu Val Lys Ser Pro Ile Lys Val
305                310                315                320

Val Gly Leu Ser Thr Leu Pro Glu Ile Tyr Glu Lys Met Glu Lys Gly
                325                330                335

Gln Ile Val Gly Arg Tyr Val Val Asp Thr Ser Lys
            340                345

<210> SEQ ID NO 78
<211> LENGTH: 587
<212> TYPE: PRT
<213> ORGANISM: Saccharomyces cerevisiae DLD1

<400> SEQUENCE: 78

Met Leu Trp Lys Arg Thr Cys Thr Arg Leu Ile Lys Pro Ile Ala Gln
 1               5                  10                 15

Pro Arg Gly Arg Leu Val Arg Arg Ser Cys Tyr Arg Tyr Ala Ser Thr
             20                 25                 30

Gly Thr Gly Ser Thr Asp Ser Ser Ser Gln Trp Leu Lys Tyr Ser Val
         35                 40                 45

Ile Ala Ser Ser Ala Thr Leu Phe Gly Tyr Leu Phe Ala Lys Asn Leu
     50                 55                 60

Tyr Ser Arg Glu Thr Lys Glu Asp Leu Ile Glu Lys Leu Glu Met Val
 65                 70                 75                 80

Lys Lys Ile Asp Pro Val Asn Ser Thr Leu Lys Leu Ser Ser Leu Asp
                 85                 90                 95

Ser Pro Asp Tyr Leu His Asp Pro Val Lys Ile Asp Lys Val Val Glu
            100                105                110

Asp Leu Lys Gln Val Leu Gly Asn Lys Pro Glu Asn Tyr Ser Asp Ala
        115                120                125

Lys Ser Asp Leu Asp Ala His Ser Asp Thr Tyr Phe Asn Thr His His
130                135                140

Pro Ser Pro Glu Gln Arg Pro Arg Ile Ile Leu Phe Pro His Thr Thr
145                150                155                160

Glu Glu Val Ser Lys Ile Leu Lys Ile Cys His Asp Asn Asn Met Pro
                165                170                175

Val Val Pro Phe Ser Gly Gly Thr Ser Leu Glu Gly His Phe Leu Pro
            180                185                190

Thr Arg Ile Gly Asp Thr Ile Thr Val Asp Leu Ser Lys Phe Met Asn
        195                200                205
```

-continued

```
Asn Val Val Lys Phe Asp Lys Leu Asp Leu Asp Ile Thr Val Gln Ala
        210                 215                 220
Gly Leu Pro Trp Glu Asp Leu Asn Asp Tyr Leu Ser Asp His Gly Leu
225                 230                 235                 240
Met Phe Gly Cys Asp Pro Gly Pro Gly Ala Gln Ile Gly Gly Cys Ile
            245                 250                 255
Ala Asn Ser Cys Ser Gly Thr Asn Ala Tyr Arg Tyr Gly Thr Met Lys
            260                 265                 270
Glu Asn Ile Ile Asn Met Thr Ile Val Leu Pro Asp Gly Thr Ile Val
        275                 280                 285
Lys Thr Lys Lys Arg Pro Arg Lys Ser Ser Ala Gly Tyr Asn Leu Asn
    290                 295                 300
Gly Leu Phe Val Gly Ser Glu Gly Thr Leu Gly Ile Val Thr Glu Ala
305                 310                 315                 320
Thr Val Lys Cys His Val Lys Pro Lys Ala Glu Thr Val Ala Val Val
            325                 330                 335
Ser Phe Asp Thr Ile Lys Asp Ala Ala Ala Cys Ala Ser Asn Leu Thr
            340                 345                 350
Gln Ser Gly Ile His Leu Asn Ala Met Glu Leu Leu Asp Glu Asn Met
            355                 360                 365
Met Lys Leu Ile Asn Ala Ser Glu Ser Thr Asp Arg Cys Asp Trp Val
    370                 375                 380
Glu Lys Pro Thr Met Phe Phe Lys Ile Gly Gly Arg Ser Pro Asn Ile
385                 390                 395                 400
Val Asn Ala Leu Val Asp Glu Val Lys Ala Val Ala Gln Leu Asn His
                405                 410                 415
Cys Asn Ser Phe Gln Phe Ala Lys Asp Asp Asp Glu Lys Leu Glu Leu
            420                 425                 430
Trp Glu Ala Arg Lys Val Ala Leu Trp Ser Val Leu Asp Ala Asp Lys
        435                 440                 445
Ser Lys Asp Lys Ser Ala Lys Ile Trp Thr Thr Asp Val Ala Val Pro
    450                 455                 460
Val Ser Gln Phe Asp Lys Val Ile His Glu Thr Lys Lys Asp Met Gln
465                 470                 475                 480
Ala Ser Lys Leu Ile Asn Ala Ile Val Gly His Ala Gly Asp Gly Asn
            485                 490                 495
Phe His Ala Phe Ile Val Tyr Arg Thr Pro Glu Glu His Glu Thr Cys
            500                 505                 510
Ser Gln Leu Val Asp Arg Met Val Lys Arg Ala Leu Asn Ala Glu Gly
        515                 520                 525
Thr Cys Thr Gly Glu His Gly Val Gly Ile Gly Lys Arg Glu Tyr Leu
    530                 535                 540
Leu Glu Glu Leu Gly Glu Ala Pro Val Asp Leu Met Arg Lys Ile Lys
545                 550                 555                 560
Leu Ala Ile Asp Pro Lys Arg Ile Met Asn Pro Asp Lys Ile Phe Lys
            565                 570                 575
Thr Asp Pro Asn Glu Pro Ala Asn Asp Tyr Arg
            580                 585
```

MICROORGANISM HAVING ENHANCED PRODUCTIVITY OF LACTIC ACID AND A PROCESS FOR PRODUCING LACTIC ACID USING THE SAME

CROSS-REFERENCE TO RELATED APPLICATIONS

This application is a U.S. National Phase Application of PCT International Application No. PCT/KR2015/005963, filed on Jun. 12, 2015, designating the United States of America and published as WO2016/199966A1 on Dec. 15, 2016.

SEQUENCE LISTING STATEMENT

The present application contains a Sequence Listing, which is being submitted via EFS-Web on even date herewith. The Sequence Listing is submitted in a file entitled "Sequence_Listing_HAN030-003APC.txt," which was created on Nov. 29, 2017, and is approximately 47 kb in size. This Sequence Listing is hereby incorporated by reference.

TECHNICAL FIELD

The present invention relates to a lactic acid-producing recombinant *Saccharomyces* sp. microorganism, and a method for producing lactic acid from the culture medium containing the microorganism by culturing the same.

BACKGROUND ART

Generally, lactic acid is an important organic acid with a wide range of applications including food additives such as food preservative, fragrance, or acidifier etc., and has been used broadly for industrial purposes such as cosmetics, chemistry, metals, electronics, fabrics, dyeing textiles, and pharmaceutical industries, etc. In addition, lactic acid is an essential ingredient of polylactic acid, one of biodegradable plastics, and thus the demand for lactic acid has been increasing significantly. It is also used as an important material for the productions of many chemical compounds including polylactic acid, acetaldehyde, polypropylene glycol, acrylic acid, 2,3-pentathione, etc. Specifically, D-type lactic acid is an essential ingredient for producing streocomplex PLA, which is an optical isomer required for the production of highly heat-resistant PLA.

Specifically, the method for producing lactic acid includes a traditional chemical synthesis and a biological fermentation process. When lactic acid is produced via the chemical synthesis, lactic acid is produced in the form of a racemic mixture consisting of 50% D-type lactic acid and 50% L-type lactic acid, and it is difficult to control the composition ratio, and thus polylactic acid produced therefrom may become an amorphous polymer having a low melting point, thereby imposing limitations on the development of their use. On the other hand, the biological fermentation process allows to selectively produce D-type lactic acid or L-type lactic acid depending on the strain used. Thus, the latter is preferred commercially because it is possible to produce a particular isoform of lactic acid.

Meanwhile, attempts have been made in order to improve the productivity of lactic acid via various gene manipulations using a *saccharomyces* sp. microorganism having D-lactic acid-producing ability, by introducing a gene of an enzyme for conversion into D-type lactic acid. Specifically, attempts have been made to improve the productivity of lactic acid by strengthening the activity of lactic acid dehydrogenase (LDH) while decreasing the activities of pyruvate decarboxylase (PDC), aldehyde dehydrogenase (ALD), and/or acetyl-CoA synthetase (ACS), and (U.S. patent application Publication Nos. 2012-021421, 2010-0248233, and 2006-0148050). However, the overall fermentation productivity was low due to the low cell growth of the lactic acid-producing strain.

DISCLOSURE

Technical Problem

Intensive efforts have been made by the present inventors in order to obtain a microorganism having improved lactic acid productivity with an efficient cell growth while decreasing the activity of PDC. As a result, it has been confirmed that strains, in which the activities of PDC isotypes were controlled and the activities of aldehyde dehydrogenase and acetyl-CoA were increased, were able to increase the lactic acid production yield and facilitate the cell growth of the strains, thereby improving the overall lactic acid fermentation productivity, and this has led to the completion of the present invention.

Technical Solution

An objective of the present invention is to provide a *Saccharomyces* sp. microorganism having improved productivity of lactic acid.

Another objective of the present invention is to provide a method for producing lactic acid using the *Saccharomyces* sp. microorganism.

Advantageous Effects

The present invention relates to using a microorganism having improved lactic acid fermentation productivity by controlling the activities of PDC isotypes, and increasing the activities of aldehyde dehydrogenase (ALD) and acetyl-CoA synthetase (ACS). Therefore, it can be extensively used in the lactic acid fermentation production industries.

BEST MODE

Figure 1:
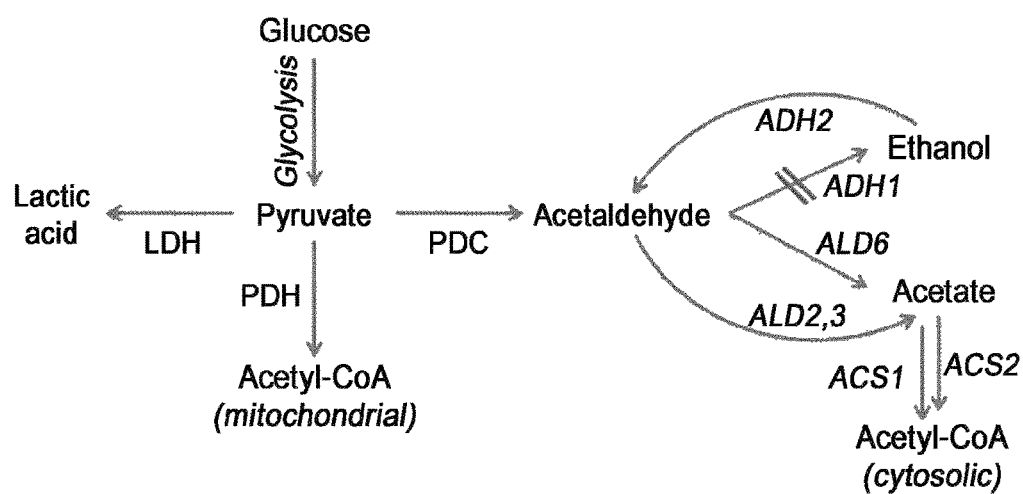
FIG. 1 is a schematic diagram illustrating the relationship between the lactic acid production pathway of a *Saccharomyces* sp. microorganism, the alcohol fermentation pathway and the acetyl-CoA production pathway.
Figure 2:
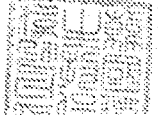
FIG. 2 is a copy of the deposit receipt of the *Saccharomyces cerevisiae* strain named CC02-0437, deposited under Budapest Treaty on Nov 22, 2013 at the Korean Culture Center of Microorganisms, and assigned Accession Number KCCM11489P.

In a first aspect of the present invention, to achieve the objectives described above, there is provided a *Saccharomyces* sp. microorganism having improved productivity of lactic acid, in which the microorganism is mutated so that (a) the activity of pyruvate decarboxylase is decreased compared to that of a non-mutated lactic acid-producing strain; and (b) the activities of aldehyde dehydrogenase and acetyl-CoA synthetase are improved compared to that of a non-mutated lactic acid-producing strain.

Generally, a lactic acid-producing *Saccharomyces* sp. microorganism produces lactic acid via lactic acid dehydrogenase (LDH) using pyruvate as a substrate. Ethanol fermentation pathway and acetayl-CoA production pathway, the representative metabolic pathways utilizing pyruvate as a common substrate, were blocked. Decreasing PDC activity may be helpful in the production of lactic acid and the yield improvement thereof, however, when the level of decrease reached a certain level, insufficient amount of cytosolic acetyl-CoA was produced, which in turn, blocked the cell growth, and thus the normal fermentation was not achieved. Accordingly, the present inventor developed a *Saccharomyces* sp. microorganism having improved productivity of lactic acid by improving the overall lactic acid fermentation productivity, in which the growth rate of the microorganism was maintained with improved lactic acid productivity yield by regulating the acetyl-CoA pathway at a minimum level.

The term "pyruvate decarboxylase (PDC) used herein refers to a protein having an activity capable of mediating a reaction responsible for producing carbonic acid and acetaldehyde from pyruvate, but is not limited to any derivative thereof or an isotype having the same activity. The protein has been known to be involved in a step of alcohol fermentation, and is mostly present in yeasts and plants. The pyruvate decarboxylase of the present invention may be intrinsically present in a *Saccharomyces* sp. microorganism, or may be PDC1, PDC5, and/or PDC6, or specifically PDC1, PDC5, and/or PDC6 of *Saccharomyces cerevisiae*, but is not limited thereto. The protein may include any variants or analogues thereof as long as they are biologically identical and have corresponding activities to the protein. The amino acid sequences of the protein may be obtained from a known database, etc., e.g., GenBank of NCBI, etc., but is not limited thereto. Specifically, PDC1 may consist of an amino acid sequence of SEQ ID NO: 71, PDC5 of an amino acid sequence of SEQ ID NO: 72, and PDC 6 of an amino acid sequence of SEQ ID NO: 73. The protein may include amino acid sequences having a homology of more than 70%, specifically more than 80%, more specifically more than 90%, and even more specifically more than 95%, to each of the above-listed amino acid sequences. Any variant of the above-listed sequences encoding the same amino acid sequences, which results from genetic code degeneracy, may also be included in the present invention.

The term "homology" used herein refers to a degree of similarity between a plurality of nucleotide sequences or amino acid sequences, and is a unit representing a sequence having the same sequences to the amino acid sequences or the nucleotide sequences of the present invention, with a probability equal to or greater than the above probability. Such homology may be determined by comparing the two given sequences with the naked eye, but rather, it may be measured using a sequence comparison program, which is easily accessible, that interprets the degree of homology by arranging the sequences to be compared side by side. The sequence comparison programs known in the art include FASTP, BLAST, BLAST2, PSIBLAST, and a software containing CLUSTAL W, etc.

Numerous examples have been reported regarding the production of lactic acid by allowing a defect in PDC1, whose exhibits a major activity in lactic acid production (Appl Microbiol Biotechnol. 2009, 82(5):883-90). In this case, since PDC6 is rarely expressed, the actual PDC activity as appears to be due to the expression of PDC5 gene. According to the reports, the defectin PDC1 alone does not hinder the cell growth of a wild-type strain, and also about 60-70% of PDC activity can be maintained compared to that of the wild-type, and thus no significant phenotypic change has been observed in the strain (J Bacteriol. 1990, 172(2): 678-685). Meanwhile, in order to maximize the lactic acid via LDH pathway, which competes with PDC for pyruvate, a strain with a simultaneous triple defect in PDC1, PDC5, and PDC6 may be prepared. In this case, lactic acid fermentation yield may be maximized but the metabolic capabilities of ethanol and acetic acid due to catabolite repression induced in the presence of glucose may be further inhibited, thereby reducing cell growth and ultimately leading to decrease in fermentation productivity (Curr Genet. 2003, 43(3): 139-160).

Since PDC6 is rarely expressed, the actual PDC activity as appears to be due to the expression of PDC5 gene. According to the reports, the defectin PDC1 alone does not hinder the cell growth of a wild-type strain, and also about 60-70% of PDC activity can be maintained compared to that of the wild-type, and thus no significant phenotypic change has been observed in the strain (J Bacteriol. 1990, 172(2): 678-685). As an alternative, a strain having a simultaneous double defect in both PDC1 and PDC5 genes, which exhibit major PDC activities in yeasts, may be prepared. In such case, lactic acid fermentation can be carried out using a sugar source such as glycogen in the absence of a co-substrate such as acetic acid or ethanol. However, it resulted in decrease in the growth rate of the yeast strain due to a rapid decrease in PDC activity, thereby reducing the fermentation productivity of lactic acid (Biosci Biotechnol Biochem. 2006, 70(5):1148-1153).

Specifically, the decrease in pyruvate decarboxlyase (PDC) activity of the present invention may i) inactivate PDC1 activity and decrease PDC5 activity; or ii) decrease PDC1 activity and inactivate PDC 5 activity.

In an exemplary embodiment of the present invention, four different strains, which include a strain with a decreased PDC5 activity by substituting the promoter of PDC5 gene, a strain that caused a defect in PDC5 gene t by recovering PDC1 activity, a strain that caused a double defect in PDC1 and PDC5 genes, and a strain that caused a triple defect in PDC1, PDC5, and PDC6 genes, were prepared based on a *Saccharomyces cerevisiae* strain in which PDC1 activity was inactivated. Among the thus prepared strains, the strain having a triple gene defect was shown to rarely undergo cell growth.

The term "aldehyde dehydrogenase (ALD)" used herein refers to a protein having an activity of mainly producing acetic acid from acetaldehyde as a protein having an activity of producing carboxylic acid or an acyl group by the oxidation of aldehyde, but is not limited to a derivative thereof or an isotype having the same activity, in the present invention. The aldehyde dehydrogenase of the present invention may be derived from a *Saccharomyces* sp. microorganism, or may be ALD2 and/or ALD3. Specifically, the protein may be ALD2 and/or ALD3 of *Saccharomyces cerevisiae*, but is not limited thereto, and may include any variant or an analogue thereof as long as they are biologically identical and have corresponding activities to the protein. The amino acid sequences of the protein may be obtained from database, etc., known in the art, e.g., GenBank of NCBI, etc., but is not limited thereto. Specifically, ALD2 may consist of an amino acid sequence of SEQ ID NO: 74, and ALD3 may consist of an amino acid sequence of SEQ ID NO: 75. The protein may include amino acid sequences having a homology of more than 70%, specifically more than 80%, more specifically more than 90%, and even more specifically more than 95%, to the amino acid sequences. Any variant of the sequences encoding the identical amino acid sequences, which results from genetic code degeneracy, may also be included in the present invention.

The term "acetyl-CoA synthetase (ACS) used herein refers to a protein having an activity of catalyzing the thioesterification of acetic acid and CoA in conjugation with an ATP decomposition reaction, but is not limited to a derivative or an isotype having the same activity in the present invention. It has been known that the protein is present in microorganisms, plants, and animals, etc. The acetyl-CoA synthetase of the present invention may be derived from a *Saccharomyces* sp. microorganism, or may be ACS1. Specifically, the protein may be ACS1 of *Saccharomyces cerevisiae*, but is not limited thereto, and may include any variant or an analogue thereof as long as they are biologically identical and have corresponding activities to the protein. The amino acid sequences of the protein may be obtained from a known database, etc., e.g., GenBank of NCBI, etc., but is not limited thereto. Specifically, ACS1 may be composed of an amino acid sequence of SEQ ID NO: 76, and may include amino acid sequences having a homology of more than 70%, specifically more than 80%, more specifically more than 90%, and even more specifically more than 95%, to the amino acid sequence. A protein mutant of the sequence encoding the identical amino acid sequences, which results from genetic code degeneracy, may also be included in the present invention.

In an exemplary embodiment of the present invention, strains, in which the activities of ALD2 and ACS, or the activities of ALD3 and ACS were increased, were prepared for the strain having a decreased PDC activity compared to that of a non-mutated microorganism. Specifically, strains having increased activities of ALD and ACS were prepared based on the strain having inactivated PDC1 via PDC1 defect and decreased PDC5 activity by substituting the gene promoter of PDC5 with a promoter having low expression ability. More specifically, strains of *Saccharomyces* sp. microorganism, in which PDC1 activity was inactivated, PDC5 activity was decreased, the activity at least one selected from the group consisting of ALD2 and ALD3 was increased, and ACS1 activity was increased, were prepared. Accordingly, it was confirmed that the growth rate of the strains, D-lactic acid production rate and the yield thereof were significantly improved.

The term "inactivation" of an enzyme activity of the present invention refers to a method for inactivating enzyme activities including any method that inhibits the expression of an enzyme, or allows the expression of an enzyme incapable of exhibiting its original activities. The method may include a partial gene deletion or a whole gene deletion caused by a homology recombination, an inhibition of an enzyme expression caused by an insertion of a foreign-derived gene into the relevant gene, an inhibition of an enzyme expression caused by a substitution or modification of a gene promoter sequence of the enzyme, or a mutation into an inactive-enzyme having a loss in its original functions caused by a substitution or modification of the enzyme, etc., but is not limited thereto.

The term "decrease" of an enzyme activity used herein refers to a method for decreasing the activity of an enzyme including any method for decreasing the expression level of an enzyme, or decreasing the activity of an enzyme being expressed. The method may include a decrease in an expression caused by a substitution or modification of a promoter sequence of the enzyme gene, or a mutation into an enzyme having decreased activity caused by a substitution or modification of the enzyme, etc., but is not limited thereto.

The term "increase" of an enzyme activity used herein refers to an insertion of a plasmid containing the genes of an enzyme, an increase in the number of gene copies encoding an enzyme on a chromosome, or an increase in an enzyme activity caused by a substitution or modification, or a mutation of a promoter sequence of an enzyme gene, etc., but is not limited thereto.

The term "yeast microorganism" used herein refers to a microorganism belonging to Eumycetes that proliferates by germination, but is not limited thereto as long as it is involved in any one of the lactic acid production pathway, alcohol production pathway, and/or acetyl-CoA production pathway. The yeast microorganism may be classified into *Saccharomyces* sp., *Pichia* sp., *Candida* sp., and *Saccharomycopsis* sp., depending on the shape of the yeast, and specifically, *saccharomyces* sp., which includes various species, may be applied in the present invention. Specifically, the microorganism may be selected from the group consisting of *Saccharomyces bayanus*, *Saccharomyces boulardii*, *Saccharomyces bulderi*, *Saccharomyces cariocanus*, *Saccharomyces cariocus*, *Saccharomyces cerevisiae*, *Saccharomyces chevalieri*, *Saccharomyces dairenensis*, *Saccharomyces ellipsoideus*, *Saccharomyces eubayanus*, *Saccharomyces exiguus*, *Saccharomyces florentinus*, *Saccharomyces kluyveri*, *Saccharomyces martiniae*, *Saccharomyces monacensis*, *Saccharomyces norbensis*, *Saccharomyces paradoxus*, *Saccharomyces pastorianus*, *Saccharomyces spencerorum*, *Saccharomyces turicensis*, *Saccharomyces unisporus*, *Saccharomyces uvarum*, and *Saccharomyces zonatus*, and more specifically, it may be *Saccharomyces cerevisiae*.

By preparing the microorganism having a decreased activity of PDC and improved activities of ALD and ACS based on *Saccharomyces cerevisiae*, a representative example of *Saccharomyces* sp., a significant increase in lactic acid production was confirmed.

The microorganism of the present invention may include alcohol dehydrogenase (ADH) that is to be further inactivated.

The term "alcohol dehydrogenase" used herein refers to a protein having an activity of catalyzing a reverse reaction responsible for producing aldehyde or ketone by removing hydrogen from alcohol, but is not limited to a derivative or an isotype having the same activity. Alcohol dehydrogenase of the present invention may be derived from *Saccharomyces* sp., or may be ADH1. Specifically, the protein may be ADH1 of *Saccharomyces cerevisiae*, but is not limited thereto, and may include any variant or an analogue thereof as long as they are biologically identical and have corresponding activities to the protein. The amino acid sequences of the protein may be obtained from a known database etc., e.g., GenBank of NCBI, etc., but is not limited thereto. Specifically, ADH1 may be composed of an amino acid sequence of SEQ ID NO: 77, and may include amino acid sequences having a homology of more than 70%, specifically more than 80%, more specifically more than 90%, and even more specifically more than 95%, to the amino acid sequence. A protein mutant of the sequence encoding the identical amino acid sequences, which results from genetic code degeneracy, may also be included in the present invention.

The microorganism of the present invention may include D-lactic acid dehyrogenase (DLD) that is further inactivated.

The term "D-lactic acid dehyrogenase" used herein, refers to a protein having an activity of producing pyruvate by anhydrization of D-lactic acid, but is not limited to an isotype having the same activity. D-lactic acid dehydrogenase of the present invention may be derived from *Saccharomyces* sp., specifically DLD1. Specifically, the protein may be DLD1 of *Saccharomyces cerevisiae*, but is not limited thereto, and may include any variant or an analogue thereof as long as they are biologically identical and have corresponding activities to the protein. The amino acid sequences of the protein may be obtained from a known database, etc., e.g., GenBank of NCBI, but is not limited thereto. Specifically, DLD1 may consist of an amino acid sequence of SEQ ID NO: 78, and may include amino acid sequences having a homology of more than 70%, specifically more than 80%, more specifically more than 90%, and even more specifically more than 95%, to the amino acid sequence. Any variant of the sequence encoding the identical amino acid sequences, which results from genetic code degeneracy, may also be included in the present invention.

In the present invention, the strains having a defect in ADH1, an enzyme involved in alcohol fermentation pathway using aldehyde as a substrate, which is further produced from pyruvate, and a defect in DLD1, an enzyme that decomposes the produced lactic acid, were used to precisely measure the changes in the lactic acid fermentation cell performances according to the regulation of acetic acid production pathway. In an exemplary embodiment of the present invention, the strains, in which the activities of PDC, ALD, and ACS were regulated, showed a significant increase in the lactic acid fermentation productivity. The results are summarized in Table 12.

In another aspect, the present invention provides a method for producing lactic acid using the microorganism of the present invention.

Specifically, in an exemplary embodiment of the present invention, the present invention provides a method for producing lactic acid including culturing the microorganism of the present invention in the culture medium and collecting lactic acid from the microorganism or the culture medium containing the microorganism.

The culturing may be performed using an appropriate medium and culturing conditions known in the art. According to the strains used, the culturing process may be readily adjusted by one of ordinary skill in the art. Examples of culturing methods include batch type, continuous type, and fed-batch type, but are not limited thereto. The media used in the culturing process should appropriately meet the requirements of a specific strain.

The medium used in the present invention contains sucrose or glucose as a main carbon source, and molasses containing a high concentration of sucrose may also be used as a carbon source. Other carbon sources may be used in an adequate amount variously. Organic nitrogen sources including peptone, yeast extract, meat extract, malt extract, corn steep liquor, and soybean wheat, and inorganic nitrogen sources including element, ammonium sulfate, ammonium chloride, ammonium phosphate, ammonium carbonate, and ammonium nitrate may be used as a nitrogen source. These nitrogen sources may be employed either singly or in combination. To the medium, phosphorus sources such as potassium dihydrogen phosphate, dipotassium hydrogen phosphate, or corresponding sodium-containing salts may be added. In addition, the medium may contain metal salts such as magnesium sulfate and iron sulfate. Further, the medium may be supplemented with amino acids, vitamins, and appropriate precursors. These media or precursors may be added to cultures by a batch type or continuous type method.

During the culturing process, compounds such as ammonium hydroxide, potassium hydroxide, phosphoric acid, and sulfuric acid may be properly added in order to adjust the pH of the culture. Further, a defoaming agent such as fatty acid polyglycol ester may be added in order to inhibit the formation of foams in the culture. In addition, to maintain the culture in an aerobic condition, oxygen or oxygen-containing gas may be injected into the culture, and to maintain the culture in anaerobic and micro-aerobic conditions, nitrogen, hydrogen, or carbon dioxide gases may be injected into the culture without injecting any gas.

The temperature of the culture may be maintained at 20 to 40° C., specifically at 25 to 35° C., and more specifically at 30° C. The culturing may be continued until a desired amount of the desired material is obtained, and specifically for 10 to 100 hours.

The lactic acid produced in the culturing processes of the present invention may be collected from the microorganism or the culture medium with/without the microorganism by a proper method known in the art, depending on the culturing method, e.g., batch type, continuous type, or fed-batch type.

MODE FOR THE INVENTION

Hereinbelow, the present invention will be described in detail with accompanying exemplary embodiments. However, the exemplary embodiments disclosed herein are only for illustrative purposes and should not be construed as limiting the scope of the present invention.

Example 1

Preparation of Lactic Acid-producing Strain

To prepare lactic acid-producing strains, *Saccharomyces cerevisiae* CEN.PK2-1 D, a representative wild type yeast obtained from EUROSCARF, was subject to genetic manipulation.

Specifically, a strain, where alcohol dehydrogenase 1 (ADH1) and pyruvate decarboxylase 1 (PDC1) were defective to minimize the loss of pyruvate to the alcohol synthesis pathway, and d-lactic acid dehydrogenase 1 (DLD1) was defective for blocking the D-type lactic acid decomposition pathway, was used as a base strain.

DLD1 is not a crucial factor that may have a direct impact on the growth improvement, but has been known as a major enzyme capable of converting D-lactic acid to pyruvate using $NAD^+$ as D-lactic acid dehydrogenase. Accordingly, a subsequent strain was constructed based on the strain having gene defects in DLD1, an enzyme that consumes the prepared lactic acid thereof, to compare a complete fermentation productivity of D-type lactic acid-producing yeast, which is intended to be prepared in the present invention. As a result, the fermentation productivity was compared.

In the present invention, a general molecular cloning was employed for the gene manipulation.

First, in order to delete ADH1 and PDC1 genes of the yeast strains, an experiment was conducted with reference to the content disclosed in the Reference by Lee T H, et al. (J. Microbiol. Biotechnol. (2006), 16(6), 979-982), using plasmids pWAL100 and pWBR100. Each insert, which was introduced into the vector plasmids, was prepared using the suitable primers (corresponding to nucleotide sequences of SEQ ID NOS: 1 to 8) via PCR.

In addition, for the deletion of DLD1 gene, HIS3, which is a marker gene, was introduced by double crossover, and made it defective. The DNA fragments used therein were prepared using primers corresponding to nucleotide sequences of SEQ ID NOS: 9 and 10.

The primers used in the gene manipulation are summarized in Table 1 below.

TABLE 1

Primers used for the production of the base yeast strain

| Primer | 5'->3' sequence |
|---|---|
| ADH1 upstream forward primer (SEQ ID NO: 1) | CGGGATCCACTGTAGCCCTAGACTTGATAGCC |
| ADH1 upstream reverse primer (SEQ ID NO: 2) | ATAAGAATGCGGCCGCTGTATATGAGATAGTTGATTGTATGCTT |
| ADH1 downstream forward primer (SEQ ID NO: 3) | GACTAGTGCGAATTTCTTATGATTTATGATTTTTATT |
| ADH1 downstream reverse primer (SEQ ID NO: 4) | ACATGCCATGgAAGCATGCACGTATACACTTGAGTAA |
| PDC1 upstream forward primer (SEQ ID NO: 5) | CGGGATCCATTATGTATGCTCTTCTGACTTTTCGT |
| PDC1 upstream reverse primer (SEQ ID NO: 6) | ATAAGAATGCGGCCGCTTTGATTGATTTGACTGTGTTATTTTGC |
| PDC1 downstream forward primer (SEQ ID NO: 7) | CGGGATCCGCGATTTAATCTCTAATTATTAGTTAAAG |
| PDC1 downstream reverse primer (SEQ ID NO: 8) | ATAAGAATGCGGCCGCTTTCAATCATTGGAGCAATCATTTTACA |
| DLD1-HIS3 upstream linking primer (SEQ ID NO: 9) | GCGTAGTTGGCCCCAACTGGTGCAGTAATACGTTTTAAGAGCTTGGTGAG |
| DLD1-HIS3 downstream linking primer (SEQ ID NO: 10) | CGTGAAGGGTGAAAAAGGAAAATCAGATACCTACATAAGAACACCTTTGG |

D-lactic acid dehydrogenase (D-LDH) specifically required for D-lactic acid production was introduced based on the strain having defects in the three genes such as ADH1, PDC1 and DLD1. D-LDH was then cloned into a vector having restriction enzyme sites of XhoI and SpeI at 5' and 3' termini, respectively, in order for 1 dhD derived from *lactobacillus plantarum* (Lb. *plantarum*) to be included between TEF1 promoter derived from *S. cerevisiae* and CYC1 terminator. In particular, the insert was prepared by double-digestion of SacI/PvuII, and the vector was blunt ended by Mungbean nuclease from the DNA fragment, which was double-digested from p-δ-neo into BamHI/NotI. Lastly, the vector was treated with Sac I to thereby obtain a vector having a SacI sticky end and BamHI derived blunt end.

The construction of pTL573 vector was completed by the ligation of the obtained vector with the insert. The plasmid pTL573 contains the IdhD gene derived from Lb. *plantarum*, and it was designed so that it may include a random insertion of multiple copies of genes into partial domain of δ-sequence among retrotrasnposable element of *S. cerevisiae* CEN.PK2-1D pdc1Δ adh1Δ dld1Δ strain. For multiple insertion of a corresponding gene, DNA fragments capable of inducing single crossover on the δ -sequence were constructed by digesting plasmid pTL573 with SalI. By introducing the DNA fragments into a parent strain via transformation, a multiple colonies were obtained from YPD plate (1% yeast extract, 2% bacto-peptone, and 2% glucose) at a maximum concentration of 5 mg/mL G418. Finally, it was confirmed that the thus-obtained strain, the Lb. *plantarum* derived D-LDH, was multiply inserted for the purpose of providing D-lactic acid-producing-ability, and was assigned CC02-0064 strain.

Example 2

Preparation of Mutant Strains Having Decreased PDC5 Activity

A mutant strain having substituted PDC5 promoter was prepared based on CC02-0064 strain prepared in Example 1. During the process, processes of cassette preparation and strain selection were conducted according to the method disclosed in Lee T. H. et al. (Development of reusable split URA3-marked knockout vectors for budding yeast, *Saccharomyces cerevisiae*. J Microbiol Biotechnol, 2006, 16:979-982).

Specifically, a total of five novel strains were prepared by substituting PDC5 promoter of the CC02-0064 strain with SCO1, SCO2, ACS1, IDP2, and FBA1 promoters, respectively, and subsequently, promoter-substituted cassettes were prepared using primers corresponding to nucleotide sequences of SEQ ID NOS: 11 to 36.

The primers used in the promoter substitution are summarized in Table 2 below.

TABLE 2

Primers used for the preparation of promoter-substituted strains

| Primers | 5'->3' sequence |
|---|---|
| F_PDC5_UP_676 (SEQ ID NO: 11) | GTCAGCATTGACACGTTCGATT |
| R_KIURA3-PDC5_UP (SEQ ID NO: 12) | TCTACCCAGAATCACTTCTTTCGAGAGATTGTCATAATC |
| F_PDC5_UP-AL_KIURA3 (SEQ ID NO: 13) | CAATCTCTCGAAAGAAGTGATTCTGGGTAGAAGATCGG |
| R_AL_KIURA3 (SEQ ID NO: 14) | GAGCAATGAACCCAATAACGAAATCTT |
| F_BR_KIURA3 (SEQ ID NO: 15) | CTTGACGTTCGTTCGACTGATGAG |
| R_PDC5_DOWN_522 (SEQ ID NO: 16) | CAAGTCAACCAAGTTAGCTGGC |
| R_SCO1p-BR _KI (SEQ ID NO: 17) | CTCTCCTAATAGACGTGGTGTCACCATGAACGACAATTCTTAA |
| F_SCO1p_500 (SEQ ID NO: 18) | CGTTCATGGTGACACCACGTCTATTAGGAGAGCCATTC |
| R_PDC5_DOWN_500-SCO1p (SEQ ID NO: 19) | AAGGTTATTTCAGACATCTTTTCTACGTTTGCTGTTTTTTC |
| F_SCO1p-PDC5_DOWN_500 (SEQ ID NO: 20) | CAGCAAACGTAGAAAAGATGTCTGAAATAACCTTAGGTAAAT |
| R_SCO2p-BR_KIURA3 (SEQ ID NO: 21) | ATCGAATAAGTAACAAGCGTGTCACCATGAACGACAATTCTTAA |
| F_SCO2p_500 (SEQ ID NO: 22) | CGTTCATGGTGACACGCTTGTTACTTATTCGATAACGC |
| R_PDC5_DOWN_500-SCO2p (SEQ ID NO: 23) | AAGGTTATTTCAGACATTTTACTCTCGCTTCCCAAATTCC |
| F_SCO2p-PDC5_DOWN_500 (SEQ ID NO: 24) | GGAAGCGAGAGTAAAATGTCTGAAATAACCTTAGGTAAAT |
| R_IDP2p-BR_KIURA3 (SEQ ID NO: 25) | TAAAAATAAATAGATAGACGTGTGTCACCATGAACGACAATTCTTAA |
| F_IDP2p_500 (SEQ ID NO: 26) | CGTTCATGGTGACACACGTCTATCTATTTATTTTTATAACTC |
| R_PDC5_DOWN_500-IDP2p (SEQ ID NO: 27) | AAGGTTATTTCAGACATTACGATTTTATATATATACGTACGTTA |
| F_IDP2p-PDC5_DOWN_500 (SEQ ID NO: 28) | CGTATATATATAAAATCGTAATGTCTGAAATAACCTTAGGTAAAT |
| R_ACS1p-BR_KIURA3 (SEQ ID NO: 29) | CTGGACGTATGTGCACAGTGTCACCATGAACGACAATTCTTAA |
| F_ACS1p_500 (SEQ ID NO: 30) | CGTTCATGGTGACACTGTGCACATACGTCCAGAATGAT |
| R_PDC5_DOWN_500-ACS1p (SEQ ID NO: 31) | AAGGTTATTTCAGACATAGCACAGTGGGCAATGTCTTTC |

TABLE 2-continued

Primers used for the preparation of promoter-substituted strains

| Primers | 5'->3' sequence |
|---|---|
| F_ACS1p-PDC5_DOWN_500 (SEQ ID NO: 32) | CATTGCCCACTGTGCTATGTCTGAAATAACCTTAGGTAAAT |
| R_FBA1p-BR_KIURA3 (SEQ ID NO: 33) | TTATTTACGTAATGACCCAGTGTCACCATGAACGACAATTCTTAA |
| F_FBA1p_500 (SEQ ID NO: 34) | CGTTCATGGTGACACTGGGTCATTACGTAAATAATGATAG |
| R_PDC5_DOWN_500-FBA1p (SEQ ID NO: 35) | AAGGTTATTTCAGACATTTTGAATATGTATTACTTGGTTATGGT |
| F_FBA1-PDC5_DOWN_500 (SEQ ID NO: 36) | CCAAGTAATACATATTCAAAATGTCTGAAATAACCTTAGGTAAAT |

The thus-prepared novel strains were assigned CC02-0167, CC02-0168, CC02-0169, CC02-0170, and CC02-0174, respectively. The corresponding strains and their genetic traits are summarized in Table 3 below.

TABLE 3

PDC5 promoter-mutated strains

| Strains | Genetic Traits |
|---|---|
| CC02-0167 | CC02-0064 PDC5 promoter:KIURA3-SCO1 promoter |
| CC02-0168 | CC02-0064 PDC5 promoter::KIURA3-SCO2 promoter |
| CC02-0169 | CC02-0064 PDC5 promoter::KIURA3-ACS1 promoter |
| CC02-0170 | CC02-0064 PDC5 promoter::KIURA3-IDP2 promoter |
| CC02-0174 | CC02-0064 PDC5 promoter::KIURA3-FBA1 promoter |

Example 3

Evaluation of Lactic Acid Fermentation for Mutant Strains Having Decreased PDC5 Activity An evaluation of lactic acid fermentation was conducted for the PDC5 promoter-mutated strains prepared in Example 2. In this regard, a specific medium was prepared for the evaluation of lactic acid fermentation.

Specifically, in order to prepare a synthetic complex media (SC media), a limiting medium for yeast, 0.67% yeast nitrogen base without amino acids serving as a base was mixed with amino acid dropout mix (Sigma) according to the protocol of the manufacturer, and added with the amino acids that were excluded in the base, as needed. In addition, 380 mg/L of leucine was added to the resultant, and uracil, tryptophan, and histidine were added at a concentration of 76 mg/L, respectively. 8% of glucose as a carbon source and 1% of CaCO₃ as a neutralizing agent were also added. The thus-prepared medium was used for the evaluation of lactic acid fermentation of the yeast strains.

Among the PDC5 promoter-mutated strains prepared in Example 2, the mutant strains substituted with a weaker promoter than the original PDC5 promoter failed to grow, whereas the mutant strains substituted with a stronger promoter showed improved growth. Specifically, the mutant strains substituted with promoters of SCO1, SCO2, IDP2 or ACS1, which are weaker promoters than PDC5 promoter, failed to grow, leaving the strains whose promoter was substituted with FBA1 promoter the only strains to be evaluated. The evaluation result of the lactic acid fermentation for CC02-0064 and CC02-0174 strains, which were measurable, is summarized in Table 4 below.

TABLE 4

Evaluation of lactic acid fermentation for PDC5 promoter-mutated strains

| | 24 hours | | | 48 hours | | | |
|---|---|---|---|---|---|---|---|
| Strain | OD | Glucose Consumed | Lactic acid | OD | Glucose Consumed | Lactic acid | Yield (%) |
| CC02-0064 | 3.9 | 15.0 | 10.9 | 8.7 | 63.4 | 41.6 | 65.7 |
| CC02-0174 | 5.7 | 25.0 | 19.8 | 9.4 | 69.9 | 47.3 | 67.7 |

As shown in the evaluation above, it was confirmed that, during the pathway promoting acetyl-CoA production, the strain where the wild-type PDC5 promoter was substituted with FBA1 promoter showed improved cell growth rate and lactic acid productivity thereof, compared to those of the original strain (CC02-0064). However, when the result of samples collected at 24 hours and 48 hours, respectively, were compared, it was confirmed that the improvements on the cell growth rate and the lactic acid productivity thereof according to the time were continued to reduce by a mere strengthening of a single PDC activity without strengthening ALD and ACS activities, which are involved in the subsequent acetyl-CoA producing pathway. In an example of the present invention, the improvement in the glucose consumption by the strengthening PDC activity was 10.3%, and the maximum lactic acid production concentration was 47.3 g/l. Accordingly, the overall improvement of the lactic acid productivity was 13.7%.

Example 4

Preparation of a Strain Having a PDC5 Gene Defect

In addition to the strain having a PDC1 gene defect and decreased PDC5 activity prepared in Example 2, a strain having a defect in PDC5 gene and decreased PDC1 activity was prepared to thereby confirm whether PDC pathway was attenuated in the corresponding strain.

Specifically, for the purpose of a PDC5 gene defect, the primers corresponding to nucleotide sequences of SEQ ID NOS: 37 to 40 were used to prepare PDC5 gene defect cassette based on the CC02-0064 strain. The defective strain was prepared by the same method described the literature of Example 1. The primers used in Example 4 are summarized in Table 5 below.

TABLE 5

Primers used for the preparation of the strain having PDC5 defects

| Primers | 5'->3' Sequence |
|---|---|
| F-ALPDC5-BamHI (SEQ ID NO: 37) | GAGCTCGGATCCAAGGAAATAAAGCAAATAACAATAACACC |
| R-ALPDC5-NotI (SEQ ID NO: 38) | ACCATGGCGGCCGCTTTGTTCTTCTTGTTATTGTATTGTGTTG |
| F-BRPDC5-SpeI (SEQ ID NO: 39) | GGATCCACTAGTGCTAATTAACATAAAACTCATGATTCAACG |
| R-BRPDC5-NcoI (SEQ ID NO: 40) | CAGCTGCCATGGTATTCTAAATAAGATGTAAGGCCTTGTAAT |

The thus-prepared strain having a PDC5 gene defect was assigned CC02-0450 (CCO2-0064, pdc5Δ).

Example 5

Preparation of PDC1 Promoter-mutated Strains Based on the Strain Having a PDC5 Defect A strain having substituted PDC1 promoter was prepared based on the CC02-0450 strain prepared in Example 4. In this regard, a strain CC02-0451 (CC02-0450, PDC1p-PDC1), where the defect in PDC1 gene was recovered, was prepared to serve as a comparative group, and a strain CC02-0452 (CC02-0450, IDP1p-PDC1) having decreased PDC1 activity was prepared to serve as an experimental group.

Each strain was prepared in such a way that the vectors of PDC1p-PDC1-CYC1t and pRS406-IDP2p-PDC1-CYC1, which were constructed by cloning a target gene cassette into a pRS406 vector without a replication origin in the yeast, to be included in the strain.

Specifically, PCR was conducted using primers having nucleotide sequences of SEQ ID NOS: 41 and 42 with chromosomal DNA of the yeast serving as a template, to thereby obtain a product including PDC1 gene. Subsequently, a sequence of CYC1 terminator was obtained using primers having nucleotide sequences of SEQ ID NOS: 43 and 44. In addition, DNA fragments connecting PDC1 and CYC1 terminator were obtained via PCR using primers corresponding nucleotide sequences of SEQ ID NOS: 41 and 44 with the PDC1 and the CYC1 terminator sequences, respectively, serving as a template. A plasmid vector of pRS406-PDC1-CYC1t was obtained by treating DNA fragments of PDC1-CYC1 terminator and pRS406 vector with SpeI and XhoI restriction enzymes followed by ligation thereof. Meanwhile, for the introduction of the promoter domain into the thus-obtained plasmid vectors, plasmid vectors, into which promoters of PDC1 and IDP2 promoters were respectively incorporated, were obtained by a primer fusion of primers having nucleotide sequences of SEQ ID NOS: 45 and 46, and 47 and 48, respectively, via PCR using chromosomal DNA as a template. DNA fragments including each promoter and pRS406-PDC1-CYC1t plasmid were digested and ligated, to thereby prepare plasmid vectors of pRS406-PDC1p-PDC1-CYC1t and pRS406-IDP2p-PDC1-CYC1t, respectively, which are plasmid required for the yeast chromosomal insertion, designed such that the gene expression is controlled by PDC1 promoter and IDP2 promoter.

The primers used in Example 5 are summarized in Table 6.

TABLE 6

Primers used for preparation of the strains having a PDC5 defect and decreased PDC1 activity

| Primers | 5'->3' Sequence |
|---|---|
| F_PDC1 (SEQ ID NO: 41) | ATAACTAGTATGTCTGAAATTACTTTGGGTAAATATTT |
| R_PDC1 (SEQ ID NO: 42) | CAAAGGAAAAGGGGCCTGTTTATTGCTTAGCGTTGGTAGCAGCA |
| F_CYC1t (SEQ ID NO: 43) | TACCAACGCTAAGCAATAAACAGGCCCCTTTTCCTTTGTCGAT |
| R_CYC1t (SEQ ID NO: 44) | ATACTCGAGGCAAATTAAAGCCTTCGAGCGTCC |
| F_PDC1p (SEQ ID NO: 45) | AAAGAGCTCCATGCGACTGGGTGAGCATATGTT |
| R_PDC1p (SEQ ID NO: 46) | ATAACTAGTTTTGATTGATTTGACTGTGTTATTTTGC |
| F_IDP2p (SEQ ID NO: 47) | AAAGAGCTC ACGTCTATCTATTTATTTTTATAACTCC |

TABLE 6-continued

Primers used for preparation of the strains having a PDC5 defect and decreased PDC1 activity

| Primers | 5'->3' Sequence |
|---|---|
| R_IDP2p (SEQ ID NO: 48) | ATAACTAGT TACGATTTTATATATATACGTACGTTAC |

The two thus-prepared plasmid vectors were digested by StuI, respectively, and inserted into the strains immediately. The final strains were assigned CC02-0451(CC02-0450, PDC1p-PDC1) and CC02-0452(CC02-0450, IDP2p-PDC1), respectively. The thus-prepared strains and their genetic traits are summarized in Table 7.

TABLE 7

Strains having PDC5 defect and decreased PDC1 activity

| Strains | Genetic Traits |
|---|---|
| CC02-0450 | CC02-0064 pdc5Δ |
| CC02-0451 | CC02-0450 PDC1p-PDC1-CYC1t |
| CC02-0452 | CC02-0450 IDP2 p-PDC1-CYC1t |

Example 6

Preparation of Strains Having Double or Triple Defects in PDC Genes

Strains having a single defect in PDC1 gene, a double defect in PDC1 and PDC5 genes, and a triple defect in PDC1, PDC5, and PDC6 genes were intended to be prepared from PDC family genes. CC02-0064 strain prepared in Example 1 was used as a strain having a single defect in PDC1 gene. A cassette for PDC5 defect was prepared using primers corresponding nucleotide sequences of SEQ ID NOS: 49 to 56, and inserted into CC02-0064 to prepare a strain having double defects in PDC1 and PDC5 genes. Subsequently, the thus-prepared strain was assigned CC02-0256. In addition, a strain having a triple defect in PDC1, PDC5, and PDC6 genes was prepared based on the strain having double defects in PDC1 and PDC5 genes using primers corresponding nucleotide sequence of SEQ ID NOS: 57 to 64 to, and was assigned CC02-0257.

The defect cassette preparation and strain selection process were conducted by the same method described in the literature disclosed in Example 1. The primers used in Example 6 are summarized in Table 8.

TABLE 8

Primers used for preparation of the strains having double or triple defects in PDC genes

| Primers | 5'->3' Sequence |
|---|---|
| F_BamHI-PDC5_UP (SEQ ID. 49) | CGGGATCCAGGCCAAGGAAATAAAGCAAATAACAA |
| R_NotI-PDC5_UP (SEQ ID NO: 50) | ATAAGAATGCGGCCGCTTTGTTCTTCTTGTTATTGTATTGT GTT |
| F_BamHI-PDC5_DOWN (SEQ ID NO: 51) | CGGGATCCGCTAATTAACATAAAACTCATGATTCAA |
| R_NotI-PDC5 DOWN (SEQ ID NO: 52) | ATAAGAATGCGGCCGCTATTCTAAATAAGATGTAAGGCCT TGTA |
| F_PDC5_UP (SEQ ID NO: 53) | AGGCCAAGGAAATAAAGCAAATAACAA |
| R_AL_K1URA3 (SEQ ID NO: 54) | GAGCAATGAACCCAATAACGAAATCTT |
| F_BR_K1URA3 (SEQ ID NO: 55) | CTTGACGTTCGTTCGACTGATGAG |
| R_PDC5_DOWN (SEQ ID NO: 56) | TATTCTAAATAAGATGTAAGGCCTTGTA |
| F_BamHI-PDC6_UP (SEQ ID NO: 57) | CGGGATCCTGTTATAGAGTTCACACCTTATTCACA |
| R_NotI-PDC6_UP (SEQ ID NO: 58) | ATAAGAATGCGGCCGCTTTGTTGGCAATATGTTTTTGCTAT ATTA |
| F_BamHI-PDC6_DOWN (SEQ ID NO: 59) | CGGGATCCGCCATTAGTAGTGTACTCAAACGAAT |

TABLE 8-continued

Primers used for preparation of the strains having double or triple defects in PDC genes

| Primers | 5'->3' Sequence |
|---|---|
| R_NotI-PDC6_DOWN (SEQ ID NO: 60) | ATAAGAATGCGGCCGCGATGCAGAATGAGCACTTGTTATTTAT |
| F_PDC6_UP (SEQ ID NO: 61) | TGTTATAGAGTTCACACCTTATTCACA |
| R_AL_KIURA3 (SEQ ID NO: 62) | GAGCAATGAACCCAATAACGAAATCTT |
| F_BR_KIURA3 (SEQ ID NO: 63) | CTTGACGTTCGTTCGACTGATGAG |
| R_PDC6_DOWN (SEQ ID NO: 64) | GATGCAGAATGAGCACTTGTTATTTAT |

The thus-prepared strains and their genetic traits are summarized in Table 9.

TABLE 9

Strains having double or triple defects in PDC genes

| Strains | Genetic traits |
|---|---|
| CC02-0256 | CC02-0064 pdc5Δ |
| CC02-0257 | CC02-0256 pdc6Δ |

Example 7

Preparation of ALD and ACS1 Overexpressing Strains

For the preparation of ALD and ACS1 over expressing strains, ALD2, ALD3, and ACS1 over expressing plasmids were prepared.

Specifically, an open reading frame (ORF) of ALD2 was prepared using primers corresponding nucleotide sequences of SEQ ID NOS: 65 and 66, an ORF of ALD3 was prepared using primers corresponding nucleotide sequences of SEQ ID NOS: 67 and 68, and an ORF of ACS1 was prepared using primers corresponding nucleotide sequences of SEQ ID NOS: 69 and 70. In addition, p415ADH-ALD2, p415ADH-ALD3, p414ADH-ACS1 and p416ADH-ACS1, which are p414ADH, p415ADH and p416ADH plasmid-based recombinant vectors, were prepared by SpeI, XhoI or EcoRI restriction enzymes. The primers used in Example 7 are summarized in Table 10 below.

TABLE 10

Primers used for he preparation of ALD and , CS1 overexpressing strains

| Primers | 5'->3' Sequence |
|---|---|
| F_SpeI_ALD2 (SEQ ID NO: 65) | CAAGCTGGCCGCTCTAGAACTAGTATGCCTACCTTGTATACTGATATCGA |
| R_XhoI_ALD2 (SEQ ID NO: 66) | ACATAACTAATTACATGACTCGAGTTAGTTGTCCAAAGAGAGATTTATGT |
| F_SpeI_ALD3 (SEQ ID NO: 67) | CAAGCTGGCCGCTCTAGAACTAGTATGCCTACCTTGTATACTGATATCGA |
| R_XhoI_ALD3 (SEQ ID NO: 68) | ACATAACTAATTACATGACTCGAGTTATTTATCCAATGAAAGATCCACAT |
| F_SpeI_ACS1 (SEQ ID NO: 69) | TCCAAGCTGGCCGCTCTAGAACTAGTATGTCGCCCTCTGCCGTACA |
| R_EcoRI_ACS1 (SEQ ID NO: 70) | TATCGATAAGCTTGATATCGAATTCTTACAACTTGACCGAATCAATTAGA |

The thus-prepared recombinant plasmids were introduced into the strains including CC02-0064, CC02-0168, CC02-0170, CC02-0256, CC02-0257, CC02-0451, and CC02-0452 via a yeast transformation by p415ADH-ALD2, p414ADH-ACS1 combination, p415ADH-ALD3, p414ADH-ACS1 combination, p415ADH-ALD2, p416ADH-ACS1 combination, or p415ADH-ALD3, p416ADH-ACS1 combination. However, no transformant was obtained in the CC02-0257 strain having triple defects in PDC genes where no PDC activity was exhibited.

The thus-prepared strains and their genetic traits and summarized in Table 11.

TABLE 11

ALD and ACS1 overexpressing strains

| Strains | Genetic Traits |
|---|---|
| CC02-0225 | CC02-0064 p415ADH, p416ADH |
| CC02-0226 | CC02-0064 p415ADH-ALD2, p416ADH-ACS1 |
| CC02-0227 | CC02-0064 p415ADH-ALD3, p416ADH-ACS1 |
| CC02-0356 | CC02-0168 p414ADH, p415ADH |
| CC02-0275 | CC02-0168 p414ADH-ACS1, p415ADH-ALD2 |
| CC02-0276 | CC02-0168 p414ADH-ACS1, p415ADH-ALD3 |
| CC02-0357 | CC02-0170 p414ADH, p415ADH |
| CC02-0437 | CC02-0170 p414ADH-ACS1, p415ADH-ALD2 |
| CC02-0278 | CC02-0170 p414ADH-ACS1, p415ADH-ALD3 |
| CC02-0444 | CC02-0256 p415ADH, p416ADH |
| CC02-0361 | CC02-0256 p415ADH-ALD2, p416ADH-ACS1 |
| CC02-0362 | CC02-0256 p415ADH-ALD3, p416ADH-ACS1 |
| CC02-0453 | CC02-0451 p414ADH, p415ADH |
| CC02-0454 | CC02-0451 p414ADH-ACS1, p415ADH-ALD2 |
| CC02-0455 | CC02-0451 p414ADH-ACS1, p415ADH-ALD3 |
| CC02-0456 | CC02-0452 p414ADH, p415ADH |
| CC02-0457 | CC02-0452 p414ADH-ACS1, p415ADH-ALD2 |
| CC02-0458 | CC02-0452 p414ADH-ACS1, p415ADH-ALD3 |

Example 8

Evaluation of Lactic Acid Fermentation for the Yeast Strains

An evaluation of lactic acid fermentation-ability for the ALD and ACS1 overexpressing strains, prepared in Example 7, was conducted.

Specifically, the yeast was inoculated into each flask containing 25 ml of the medium, prepared in Example 3 for the purpose of lactic acid fermentation evaluation and was cultured under aerobic condition at 30□ for 71 hours. The amount of D-type lactic acid present in the fermented broth was analyzed, and an enzymatic analysis (Acetic acid, R-Biopharm, Germany) was conducted to determine the amount of acetic acid present therein.

The above experiment results are summarized in Table 12 below.

TABLE 12

Evaluation of the growth rate, lactic acid fermentation, by-products, and production yield, etc., for the ALD and ACS overexpressing strains

| Strains | Final OD | Initial glucose (g/L) | Residual glucose (g/L) | Acetate (g/L) | D-lactic acid (g/L) | Yield (g/g) | Productivity (g/l·h) |
|---|---|---|---|---|---|---|---|
| CC02-0225 | 9.3 | 88 | 10 | 2.87 | 41.1 | 0.53 | 0.579 |
| CC02-0226 | 9.3 | 83 | 10.5 | 2.91 | 42.4 | 0.59 | 0.597 |
| CC02-0227 | 10.1 | 84 | 9.5 | 2.91 | 41.8 | 0.56 | 0.589 |
| CC02-0356 | 6.9 | 88 | 26 | 0.02 | 27.6 | 0.45 | 0.389 |
| CC02-0275 | 11.6 | 88 | 11.5 | 0.01 | 47.6 | 0.62 | 0.670 |
| CC02-0276 | 10.6 | 88 | 11 | 0.01 | 46.8 | 0.61 | 0.659 |
| CC02-0357 | 12.2 | 88 | 13 | 0.04 | 38.1 | 0.51 | 0.537 |
| CC02-0437 | 17.8 | 88 | 1 | 0.03 | 58.6 | 0.67 | 0.825 |
| CC02-0278 | 18.8 | 88 | 0 | 0.02 | 56.9 | 0.66 | 0.801 |
| CC02-0453 | 9.8 | 88 | 8.5 | 2.2 | 38.9 | 0.49 | 0.548 |
| CC02-0454 | 10.2 | 88 | 8.1 | 2.4 | 39.5 | 0.49 | 0.556 |
| CC02-0455 | 9.2 | 88 | 8.8 | 2.1 | 40 | 0.51 | 0.563 |
| CC02-0456 | 12 | 88 | 10.1 | 0.02 | 38.5 | 0.49 | 0.542 |
| CC02-0457 | 18.1 | 88 | 0 | 0.02 | 55.8 | 0.63 | 0.786 |
| CC02-0458 | 18.5 | 88 | 0 | 0.02 | 56.5 | 0.64 | 0.800 |

As verified in Table 12, the strains having decreased PDC5 activity by IDP2 promoter or SCO2 promoter had a dramatic reduction in the accumulation of the acetate, a by-product, i.e., little detection of acetate was confirmed, compared to the strain with normal PDC5 activity. In such case, the final cell concentration of the strains, in which the activities of ALD and ACS were not increased, tended to decrease according to the PDC5 promoter substitutions. On the contrary, the strains, where the PDC5 expression was reduced and the activities of ALD and ACS were increased, showed an increase in the final cell concentration. Accordingly, the improvement in the cell growth was confirmed. Specifically, the strains of CC02-0437 and CC02-0278 having increased ALD and ACS activities prepared based on the CC02-0170 strain, where PDC5 promoter was substituted with IDP2, showed improved growth rate, D-lactic acid concentration of production, production yield thereof, and fermentation productivity as increasing in the ALD and ACS activities.

In summary, the strain where PDC5 was substituted with a weak expression of IDP2 had a reduction in acetate accumulation, and the final OD was 1.3 times higher compared to the strain exhibiting normal expression of PDC5. In addition, it was confirmed that, when ALD and ACS were co-expressed under the control of the ADH1 promoter, the glucose consumption and the rate thereof were increased, and finally, the percentage yield was increased from 56% or %59% to 66% or 67%, respectively, showing improved yield.

Specifically, by comparing the two kinds of promoters applied to the weak expression of PDC5, it was confirmed that, the lactic acid productivity was improved in both strains having SCO2 promoter and IDP2 promoter, respectively. However, the strain having IDP2 promoter may be considered as the most optimized form of a strain in terms of the overall cell concentration, the glucose consumption, and the rate thereof.

Accordingly, the CC02-0437 strain, which was confirmed on its growth rate, D-lactic acid-producing concentration, yield, and fermentation productivity, was deposited at Korean Culture Center of Microorganisms (KCCM), an international depository authority under the Budapest Treaty, on Nov. 22, 2013 (Accession No. KCCM 11489P).

Example 9

Evaluation of Lactic Acid Fermentation for the Yeast Strain Having Double Defects in PDC1 and PDC5 Genes, and Increase in ALD and ACS Activities Since the effects of the cell growth and the yield improvements resulted from the decreased PDC5 activity have been clearly confirmed, an evaluation was undertaken to determine the effects of additional PDC gene defect in lactic acid production. The evaluation method for each strain was identical to the method described in Example 8, and the culturing was conducted for 74 hours.

The thus-obtained experiment results are summarized in Table 13 below.

TABLE 13

The evaluation results of lactic acid fermentation for the strains having double defects in PDC1 and PDC5 genes

| Strains | Final OD | Initial Glucose (g/L) | Residual Glucose (g/L) | Acetate (g/L) | D-lactic acid (g/L) | Yield (g/g) | Productivity (g/l · h) |
|---|---|---|---|---|---|---|---|
| CC02-0444 | 3.2 | 78.5 | 52 | 0.10 | 20.8 | 78.5 | 0.281 |
| CC02-0361 | 3.9 | 78.5 | 49 | 0.05 | 25.4 | 86.3 | 0.343 |
| CC02-0362 | 3.8 | 78.5 | 51 | 0.08 | 22.8 | 82.8 | 0.308 |

As confirmed in Table 13, the acetate concentration was clearly reduced in the strains having double defects in PDC1 and PDC5 genes, however, a reduction in the D-lactic acid concentration of production was also observed due to the reduction in the cell growth and the glucose consumption. In addition, the strain where the PDC pathway is almost inactivated, which was resulted from the double defects in PDC1 and PDC5 genes, did not have any improvement in the cell growth, the glucose consumption, and the productivity thereof, although the strain exhibited increased activities of ALD and ACS.

Example 10

Evaluation of Lactic Acid Fermentation for the Strains, where PDC Pathway is Attenuated, Using Sucrose For the purpose of a fermentation evaluation using sucrose, the lactic acid-producing yeast strains, where PDC pathway is attenuated, the identical strains evaluated in Example 8 and 9 were used to confirm the effect of the lactic acid production. In this regard, sucrose was employed as a carbon source instead of glucose. The evaluation method was performed in the same manner as Example 8.

The thus-obtained experiment results are summarized in Table 14 below.

TABLE 14

The evaluation results of lactic acid fermentation for the strains having double defects in PDC1 and PDC5 genes or decreased PDC5 activity

| Strains | Final OD | Initial Glucose (g/L) | Residual Glucose (g/L) | Acetate (g/L) | D-lactic acid (g/L) | Yield (g/g) | Productivity (g/l · h) |
|---|---|---|---|---|---|---|---|
| CC02-0225 | 5.15 | 91.5 | 27.5 | 1.95 | 25.19 | 39.36 | 0.34 |
| CC02-0226 | 6.9 | 91.5 | 15 | 1.92 | 30.89 | 40.38 | 0.42 |
| CC02-0227 | 6.18 | 91.5 | 15 | 1.98 | 29.59 | 38.68 | 0.40 |
| CC02-0356 | 1.6 | 91.5 | 26.75 | 0.02 | 11.72 | 18.11 | 0.16 |
| CC02-0275 | 1.88 | 91.5 | 21.75 | 0.02 | 13.79 | 19.77 | 0.19 |
| CC02-0276 | 2.2 | 91.5 | 18.25 | 0.01 | 16.04 | 21.9 | 0.22 |
| CC02-0357 | 2.78 | 91.5 | 22 | 0.03 | 17.08 | 24.58 | 0.23 |
| CC02-0437 | 12.15 | 91.5 | 7.75 | 0.02 | 44.65 | 53.31 | 0.60 |
| CC02-0278 | 11.88 | 91.5 | 6.25 | 0.01 | 43.84 | 51.43 | 0.60 |
| CC02-0444 | 2.45 | 91.5 | 37 | 0.02 | 21.94 | 40.25 | 0.30 |
| CC02-0361 | 2.5 | 91.5 | 18.25 | 0.02 | 21.73 | 29.66 | 0.29 |
| CC02-0362 | 3.08 | 91.5 | 15.25 | 0.02 | 24.92 | 32.67 | 0.34 |

The use of sucrose instead of glucose for the strains, used in the same manner as in Examples 8 and 9, allowed for improved effects of the growth and fermentation yield by increasing the activities of ALD and ACS in the strains where PDC pathway is attenuated, showing the same pattern of results as the strains in Example 8 where glucose was employed as a carbon source. Accordingly, the present invention confirms that the improved effects of fermentation yield and growth due to the decreased PDC activity and increased ALD and ACS activities, which were confirmed in the present invention, are not limited to the type of sugar used.

To summarize the above results, it was confirmed that, when the strains were mutated in such a way that PDC pathway was attenuated, and the activities of ALD and ACS were improved compared to that of the non-mutated strains, the lactic acid production was increased, and the growth rate thereof was maintained simultaneously.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. An isolated *Saccharomyces cerevisiae* microorganism having enhanced productivity of lactic acid, wherein the microorganism is modified so that:
   a) the activity pyruvate decarboxylase (PDC) of the microorganism is decreased compared to that of a non-modified lactic acid-producing strain, wherein the activity of PDC is decreased by (i) inactivating PDC1 activity and decreasing PDC5 activity; or (ii) decreasing PDC1 activity and inactivating PDC 5 activity; and b) the activities of aldehyde dehydrogenase (ALD) and acetyl-CoA synthetase (ACS) of the microorganism are enhanced compared to that of the non-modified lactic acid-producing strain, wherein the activities are enhanced by insertion of a plasmid containing the genes of an enzyme, an increase in the number of gene copies encoding an enzyme on a chromosome, or an increase in an enzyme activity caused by a substitution or modification, or a mutation of a promoter sequence of an enzyme gene.

2. The microorganism according to claim 1, wherein the aldehyde dehydrogenase is at least one selected from the group consisting of ALD2 and ALD 3, and the acetyl-CoA synthetase is ACS1.

3. The microorganism according to claim 1, wherein alcohol dehydrogenase (ADH) is further inactivated.

4. The microorganism according to claim 1, wherein D-lactic acid dehydrogenase (DLD) is further inactivated.

5. A method for producing lactic acid comprising:
a) culturing the microorganism according to claim 1 in the culture medium; and
b) recovering lactic acid from the culture medium or the microorganism in step a).

6. A method for producing lactic acid comprising:
a) curing the microorganism according to claim 2 in the culture medium; and
b) recovering lactic acid from the culture medium or the microorganism in step a).

7. A method for producing lactic acid comprising:
a) uring the microorganism according to claim 3 in the culture medium; and
b) recovering lactic acid from the culture medium or the microorganism in step a).

8. A method for producing lactic acid comprising:
a) culturing the microorganism according to claim 4 in the culture medium; and
b) recovering lactic acid from the culture medium or the microorganism in step a).

* * * * *